(12) United States Patent
Rudek et al.

(10) Patent No.: US 9,412,216 B2
(45) Date of Patent: Aug. 9, 2016

(54) MULTI-CHAMBERED EARPLUG DISPENSER

(71) Applicant: 3M INNOVATIVE PROPERTIES COMPANY, St. Paul, MN (US)

(72) Inventors: David M. Rudek, Dusseldorf (DE); Guenter M. Zilligen, Grevenbroich (DE); Joerg R. Purfuerst, Schwabisch Hall (DE)

(73) Assignee: 3M Innovative Properties Company, St. Paul, MN (US)

( * ) Notice: Subject to any disclaimer, the term of this patent is extended or adjusted under 35 U.S.C. 154(b) by 126 days.

(21) Appl. No.: 14/138,612

(22) Filed: Dec. 23, 2013

(65) Prior Publication Data

US 2015/0179018 A1    Jun. 25, 2015

(51) Int. Cl.
| | |
|---|---|
| *G07F 11/00* | (2006.01) |
| *B65H 3/60* | (2006.01) |
| *G07F 11/54* | (2006.01) |
| *A61F 15/00* | (2006.01) |

(52) U.S. Cl.
CPC .............. *G07F 11/54* (2013.01); *A61F 15/001* (2013.01)

(58) Field of Classification Search
CPC .................................. G07F 11/54; G07F 11/56
USPC .................. 221/186, 203, 256, 277, 265, 263
See application file for complete search history.

(56) References Cited

U.S. PATENT DOCUMENTS

| | | |
|---|---|---|
| 920,931 A | 5/1909 | Donnelly |
| 1,651,605 A | 12/1927 | Kuhn |
| 1,982,273 A | 11/1934 | Vogel |
| 2,176,232 A | 10/1939 | Warren |
| 2,243,335 A | 5/1941 | Elliott |

(Continued)

FOREIGN PATENT DOCUMENTS

| | | |
|---|---|---|
| AU | 2006-201162 | 4/2006 |
| CA | 92208 | 3/1905 |

(Continued)

OTHER PUBLICATIONS

3M™ E-A-R™ One Touch™ Earplug Dispenser product information webpage obtained from the internet on Jul. 16, 2014: http://solutions.3m.com/wps/portal/3M/en_US/3M-PPE-Safety-Solutions/Personal-Protective-Equipment/Products/Product-Catalog/~/Dispensers-Refills?N=8690968+5158346+3294529207+3294349995+4294886830&rt=rud.

*Primary Examiner* — Rakesh Kumar
(74) *Attorney, Agent, or Firm* — Kenneth B. Wood

(57) ABSTRACT

A manually operable dispenser for dispensing disposable earplugs. The dispenser includes a housing, index body, and plate. The housing forms an opening for receiving earplugs from a container. The index body includes a handle, hub, guide cone and shield. The hub forms opposing major faces and a plurality of circumferentially arranged bores. The guide cone projects from the upper major face, tapering in diameter to a leading end. A base of the shield is disposed above the leading end opposite the upper major face. A wall of the shield projects radially outwardly to an edge having a diameter greater than a diameter of the leading end. The shield and the handle are rotationally affixed. The hub is rotatably mounted within the opening. The plate is connected to the housing and forms a dispensing aperture. A manually-applied rotational force at the handle selectively aligns individual ones of the bores with the dispensing aperture.

16 Claims, 23 Drawing Sheets

(56) References Cited

U.S. PATENT DOCUMENTS

| | | | |
|---|---|---|---|
| 2,535,928 A | 12/1950 | Ives | |
| 2,630,245 A * | 3/1953 | Maier | A47F 1/03 221/264 |
| 2,742,200 A | 4/1956 | Marx | |
| 2,772,811 A | 12/1956 | Schaef | |
| 2,880,906 A | 4/1959 | Probasco | |
| 2,886,209 A | 5/1959 | Lermer | |
| 3,079,051 A | 2/1963 | Clark | |
| 3,128,011 A * | 4/1964 | Bleiman | G07F 11/44 221/154 |
| 3,246,806 A * | 4/1966 | McBride, Jr. | A01C 9/08 221/265 |
| 3,730,387 A | 5/1973 | McConnell | |
| 3,785,525 A * | 1/1974 | Handeland | C02F 1/687 221/15 |
| 3,811,599 A | 5/1974 | O'Connor | |
| 3,885,703 A | 5/1975 | Neavin | |
| 3,894,657 A * | 7/1975 | Eckmayr | A63B 47/002 221/265 |
| 4,191,308 A | 3/1980 | Allen | |
| 4,273,254 A | 6/1981 | Cuppleditch | |
| 4,515,063 A | 5/1985 | Lee | |
| 4,782,981 A | 11/1988 | Schuster | |
| 5,014,877 A | 5/1991 | Roos | |
| 5,280,845 A * | 1/1994 | Leight | G07F 11/44 221/1 |
| 5,285,925 A | 2/1994 | Leight | |
| 5,322,185 A * | 6/1994 | Leight | A61F 11/08 221/1 |
| 5,372,278 A | 12/1994 | Leight | |
| 5,791,515 A | 8/1998 | Khan | |
| 5,794,816 A | 8/1998 | Pliler | |
| D413,465 S | 9/1999 | Scholey | |
| D414,359 S | 9/1999 | Scholey | |
| 5,954,229 A | 9/1999 | Scholey | |
| D424,340 S | 5/2000 | Fleming | |
| 6,241,120 B1 * | 6/2001 | Scholey | A61F 11/08 221/186 |
| 6,283,339 B1 | 9/2001 | Morrow | |
| 6,299,019 B1 * | 10/2001 | Leight | A61F 15/001 221/186 |
| 6,604,653 B2 * | 8/2003 | Millar | G07F 11/44 221/203 |
| 7,097,068 B2 | 8/2006 | Limback | |
| 7,175,046 B2 | 2/2007 | Yao | |
| 7,556,176 B2 * | 7/2009 | Yao | G07F 11/007 221/155 |
| 7,810,673 B2 | 10/2010 | Lancesseur | |
| 7,992,748 B2 * | 8/2011 | Lawrence | G07F 11/54 221/203 |
| 2006/0006189 A1 * | 1/2006 | Curtolo | G21C 19/202 221/178 |
| 2008/0116219 A1 * | 5/2008 | Lawrence | G07F 11/54 221/265 |
| 2015/0027286 A1 * | 1/2015 | Yuyama | G07F 11/66 83/105 |
| 2015/0179018 A1 * | 6/2015 | Rudek | A61F 15/001 221/186 |

FOREIGN PATENT DOCUMENTS

| | | | |
|---|---|---|---|
| EP | 1035035 | 9/2000 | |
| EP | 1074236 A2 * | 2/2001 | ............ A61F 15/001 |
| EP | 1739638 | 1/2007 | |
| EP | 1772077 | 4/2007 | |
| WO | WO 94-09456 | 4/1994 | |
| WO | WO 9409456 A1 * | 4/1994 | ............ A61F 15/001 |

* cited by examiner

MULTI-CHAMBERED EARPLUG DISPENSER

BACKGROUND

The present disclosure relates to product dispensers. More particularly, it relates to manually operable dispensers for storing and dispensing disposable earplugs.

Disposable earplugs are routinely used in a wide variety of settings. In many instances, such as industrial or manufacturing environments, it is highly desirable to have a large quantity of disposable earplugs readily available at all times. Conventionally, disposable earplugs are made available in bulk form, for example by way of a large open box in which the earplugs are loosely maintained. Workers (or other users) simply reach into the box and retrieve earplugs as needed. While viable, the open box format has several distinct drawbacks. For example, a worker will invariably retrieve more than two earplugs when reaching into the box, with the extra, un-needed earplugs often times discarded without being used. Moreover, contaminants in the working environment and/or carried by the worker's hand can be introduced into the open box, leading to possible hygienic concerns.

To address the above concerns, various disposable earplug dispensers have been devised. Typically, the dispenser loosely stores a large, bulk supply of disposable earplugs and provides a manually operable mechanism intended to dispense or vend earplugs one at a time. The dispensing mechanism is conventionally a rotary type, including a wheel forming a series of discrete holes. In theory, earplugs for the bulk supply self-load into respective ones of the holes and then individually dispense from the mechanism, under the force of gravity, with rotation of the wheel. Notably, rotary dispensing mechanisms sometimes employed with earplug dispensers are akin to those found with some medication capsule dispensers or other devices intended to store and individually dispense (or vend) small, hard objects (e.g., gumballs). Given the general similarities between the size and shape of medicinal capsules and disposable earplugs, the apparent usefulness of this rotary mechanism format is well-based. However, certain physical characteristics unique to disposable earplugs present distinct concerns not fully addressed by conventional rotary-type dispensing mechanisms.

For example, some types of disposable earplugs are formed of a slow-recovery foam material, open cell or closed surface and, unlike hard objects, are compressible. Further, most disposable earplugs exhibit some degree of tackiness at their outer surface. These unique characteristics make it difficult for a conventional rotary-type dispensing mechanism to accurately and consistently dispense only a single earplug with each user-caused wheel rotation. Instead, two (or more) earplugs will self-load into a single dispensing hole and subsequently dispense in tandem; alternatively, the bulk supply will overtly prevent any one earplug from self-loading into a dispensing hole. Further, malfunctions can be prevalent, with the compressible earplugs easily becoming lodged between various moving components of the dispensing mechanism.

In light of the above, a need exists for disposable earplug dispensers, and related manually operable dispensing mechanism, that accurately dispense earplugs one at a time with minimal instances of jamming or other malfunctions.

SUMMARY

Some aspects in accordance with principles of the present disclosure relate to a manually operable dispenser for dispensing disposable earplugs from a container of earplugs. The dispenser includes a housing, an index body, and a plate. The housing forms an opening for receiving earplugs from a container. The index body includes a handle, a hub, a guide cone and a shield. The handle terminates a lower end. The hub projects radially outwardly from the handle opposite the lower end, and forms opposing, upper and lower major faces. Further, the hub forms a plurality of circumferentially arranged bores each configured to receive an earplug. The guide cone projects from the upper major face, tapering in diameter to a leading end. The shield includes a base and a shield wall. The base is disposed above the leading end opposite the upper major face. The shield wall projects radially outwardly from the base to a perimeter edge having a diameter greater than a diameter of the leading end. The shield and the handle are rotationally affixed. The hub is rotatably mounted within the opening. The plate is connected to the housing proximate the lower major face and forms a dispensing aperture. The dispenser is configured such that a manually-applied rotational force at the handle selectively aligns individual ones of the bores with the dispensing aperture. In some embodiments, a first chamber is established below the shield, and a second chamber is established above the shield. With these constructions, the shield protects earplugs in the first chamber from a collective weight of earplugs in the second chamber, allowing earplugs in the first chamber to more easily load into an open one of the bores. In some embodiments, the housing includes a sleeve and a guide wall. Upon final assembly, an inner edge of the guide wall is proximate the bores, with the guide wall and the guide cone configured in tandem to encourage earplugs to load into open bores in a lengthwise direction or orientation.

DETAILED DESCRIPTION

Figure 1A:
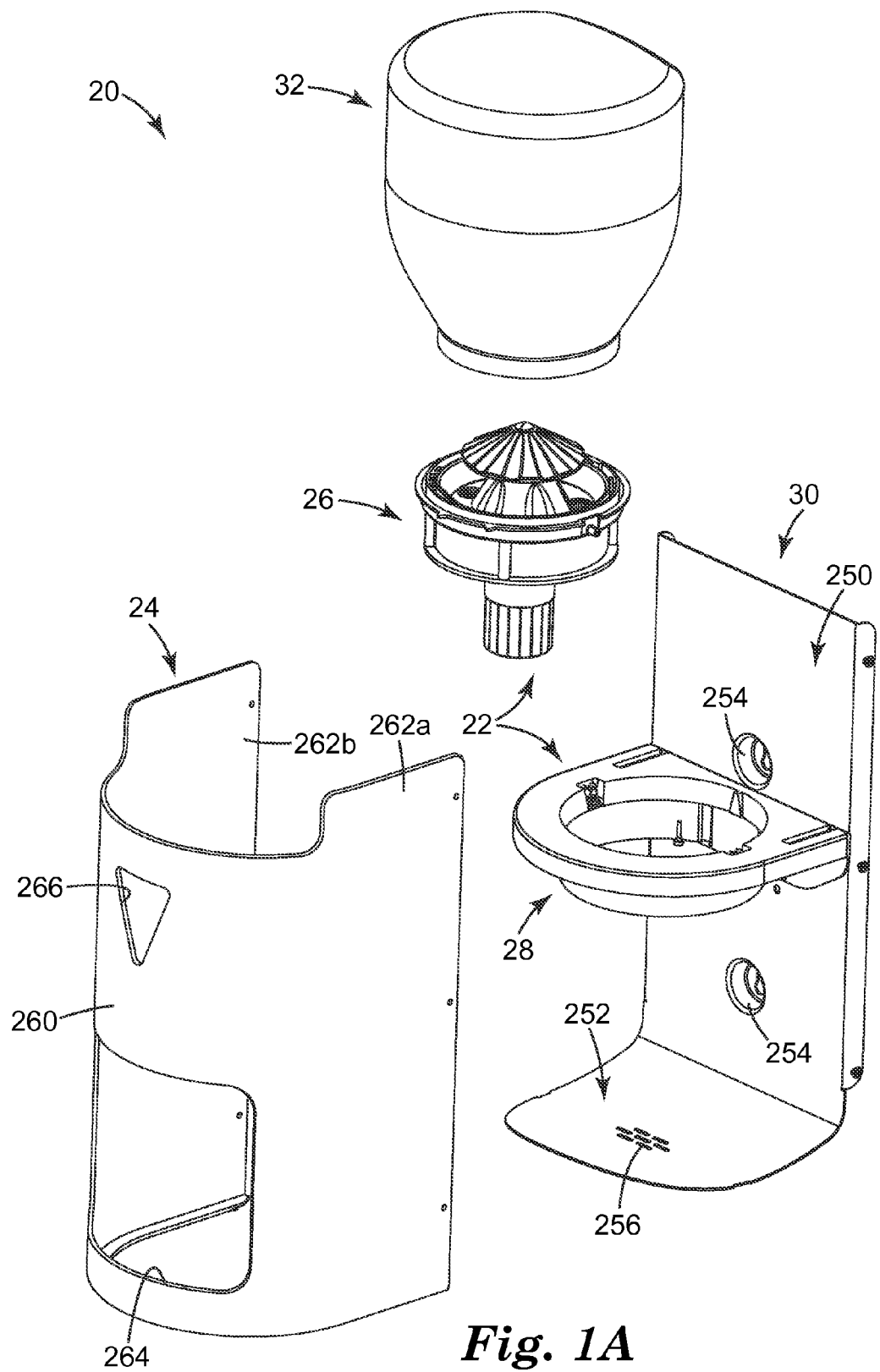
FIG. 1A is a perspective, exploded view of an earplug dispenser in accordance with principles of the present disclosure.
Figure 1B:
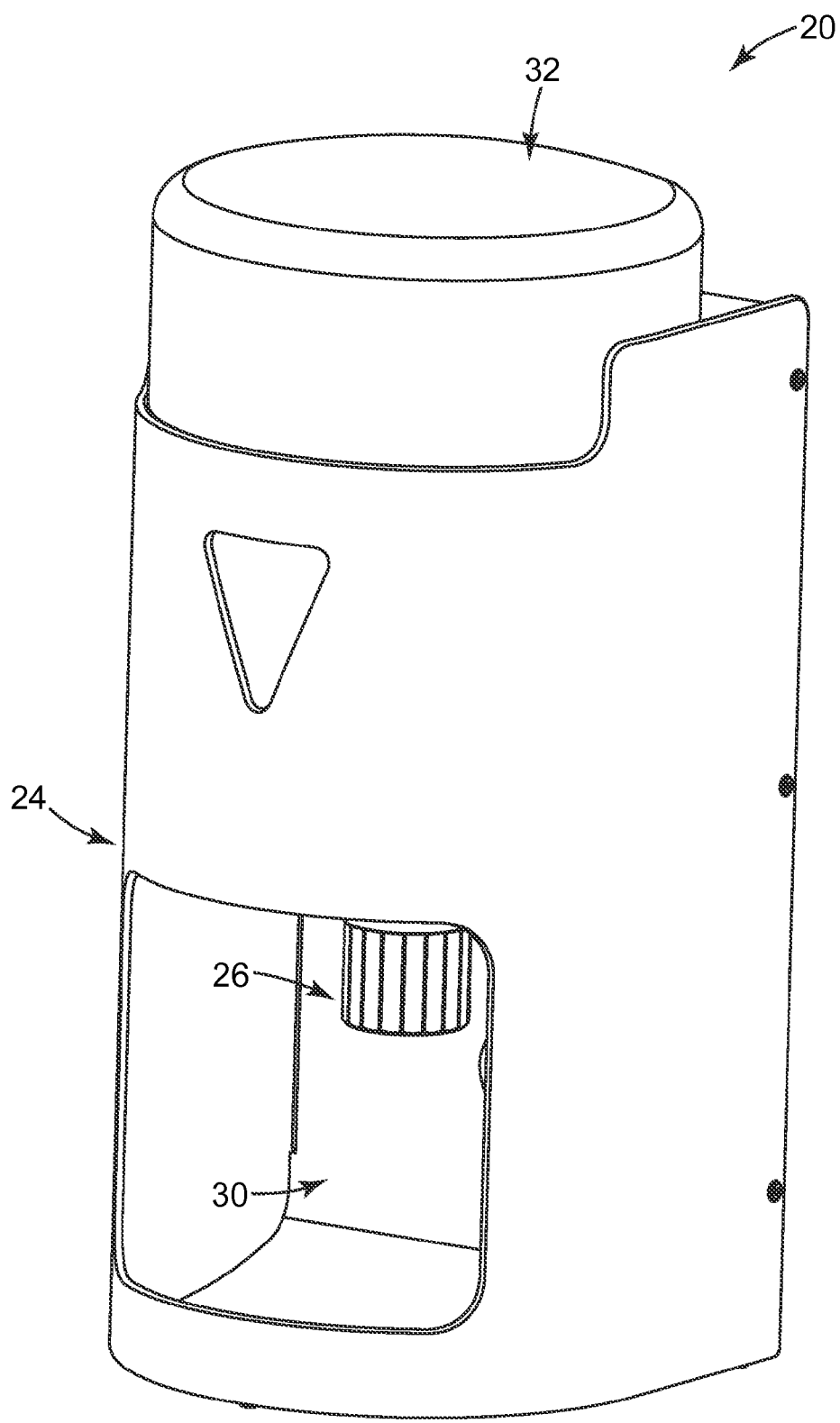
FIG. 1B is a perspective view of the dispenser of FIG. 1A upon final assembly.

One embodiment of an earplug dispenser 20 in accordance with principles of the present disclosure is shown in FIGS. 1A and 1B. The dispenser 20 includes a dispensing unit 22 and an optional cover 24. The dispensing unit 22, in turn, includes a dispensing mechanism 26 and a frame 28 maintained by an optional stand 30. Details on the various components are provided below. In general terms, however, the dispensing mechanism 26 is configured to receive a container 32 containing a bulk supply of disposable earplugs (not shown), and is manually operable to individually dispense earplugs from the bulk supply. The frame 28 retains the dispensing mechanism 26, with the optional stand 30 supporting the frame 28, and thus the dispensing mechanism 26, relative to an installation surface (e.g., wall, table top, etc.). Where provided, the cover 24 partially shields the individual earplugs from the surrounding environment as they are released from the dispensing mechanism 26. The dispenser 20, and in particular the dispensing mechanism 26, is configured to interface with and accurately dispense compressible, tacky surface earplugs with minimal occurrences of mechanism jamming.

Figure 2:
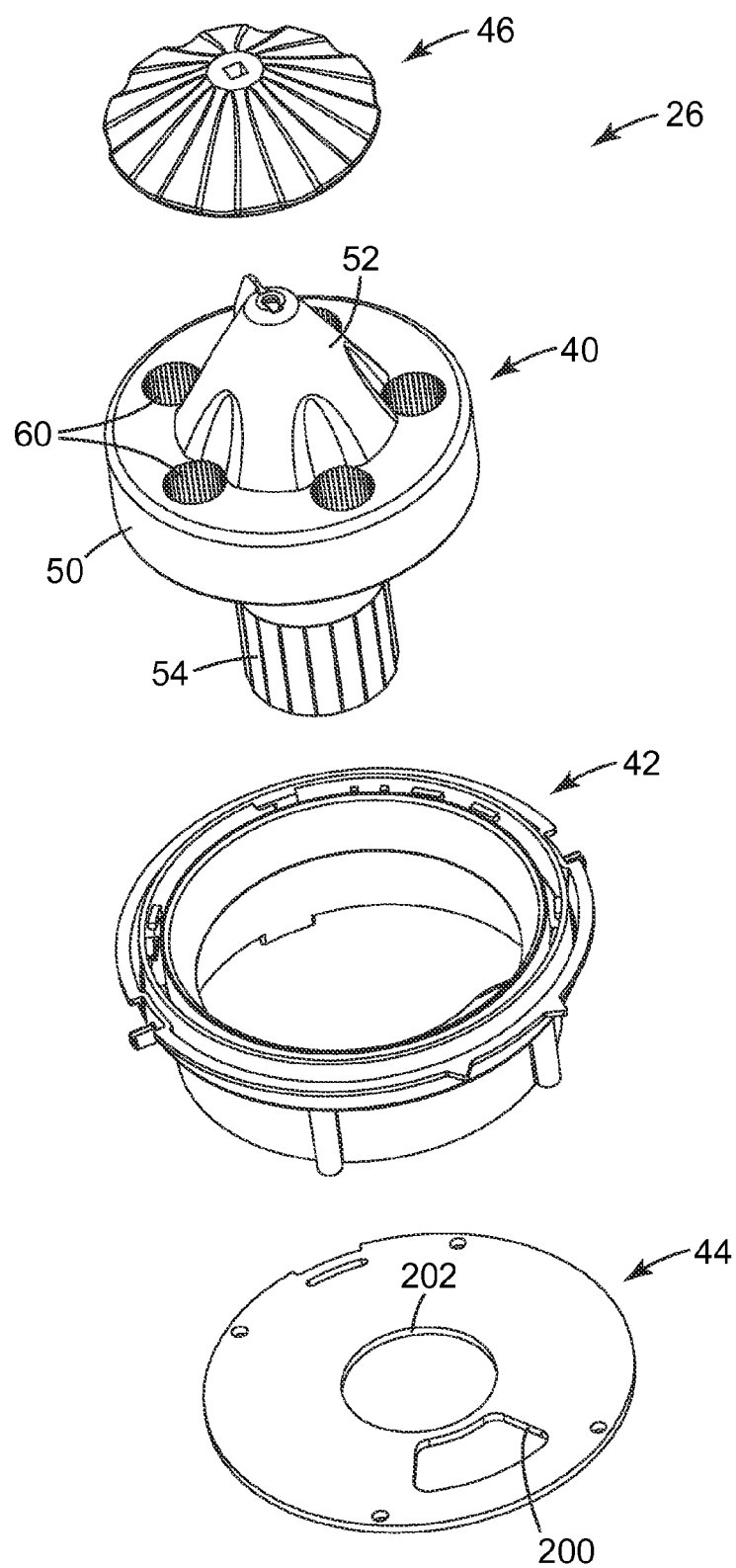
FIG. 2 is an exploded, perspective view of a dispensing mechanism useful with the dispenser of FIG. 1A.

One embodiment of the dispensing mechanism 26 is shown in greater detail in FIG. 2, and includes an index body 40, a housing 42, a plate 44 and an optional shield 46. The index body 40 is configured for rotatable coupling with the housing 42, and includes or defines a hub 50, a guide cone 52 and a handle 54. With reference to FIGS. 3A-3D, the guide cone 52 and the handle 54 project in opposite directions from the hub 50 along a longitudinal axis A of the index body 40.

In some embodiments, the hub 50 includes a platform 56 that extends radially relative to the longitudinal axis A and terminates at an annular outer wall 58. A plurality of bores 60 are formed in the platform 56, and are each sized and shaped to selectively receive a single earplug (not shown). As best reflected by the view of FIG. 3B, the bores 60 are circumferentially aligned, and in some embodiments are equidistantly spaced from each other. While the views reflect the hub 50 as providing five of the bores 60, any other number, either greater or lesser, is equally acceptable.

The bores 60 are arranged to extend in the longitudinal direction (e.g., a central axis of each of the bores 60 is substantially parallel (e.g., within 5 degrees of a truly parallel relationship) with the longitudinal axis A), and are open to opposing major faces of the hub 50. Relative to the orientation of FIGS. 3A and 3C, then, earplugs (not shown) are initially loaded into the bores 60 from "above" the platform 56, and are dispensed or released to a location "below" the hub 50. In this regard, the platform 56 defines an upper major face of the hub 50. In some embodiments, the hub 50 can have a generally hollow construction, with the annular outer wall 58 defining a lower major face 62 of the hub 50 opposite the platform 56. In other embodiments, the hub 50 can have a more solid construction. Regardless, and as described in greater detail below, individual earplugs will self-load into each of the bores 60 at the platform 56, followed by gravity-induced release of an individual earplug from the corresponding bore 60 in a direction of the lower major face 62. The bores 60 can each have the cylindrical shape as shown. In other embodiments, the bores 60 can have a tapering shape, either increasing or decreasing in diameter in extension from the platform 56. In yet other embodiments, the bores 60 can be non-circular in transverse cross-section, for example having an oval-like perimeter shape.

Figure 4A:
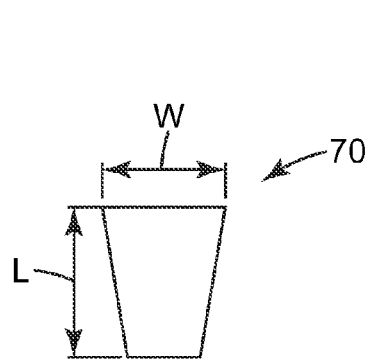
FIG. 4A is a simplified side view of a disposable earplug.
Figure 4B:
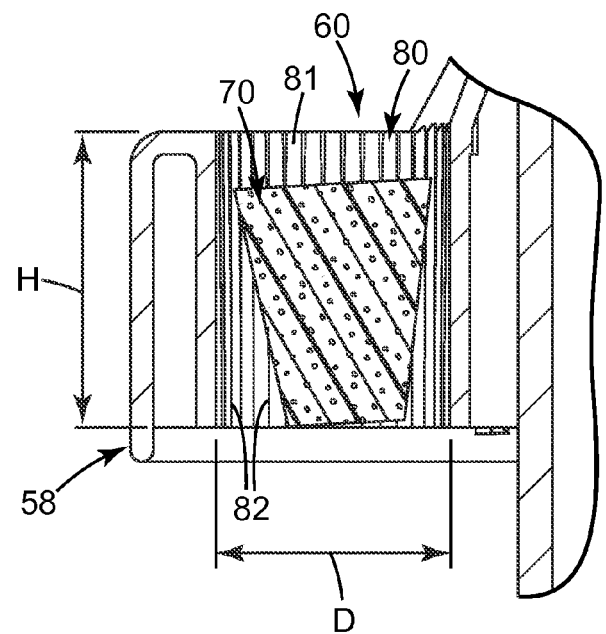
FIGS. 4B and 4C are enlarged, cross-sectional views of a portion of the index body of FIG. 3A, and illustrate an interface between a disposable earplug and a bore provided with the index body.
Figure 4C:
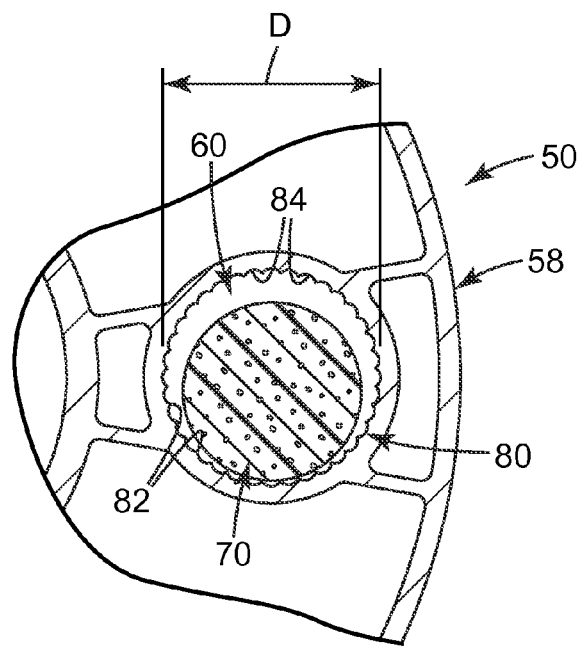

The bores 60 are generally sized and shaped to promote temporary retention of an individual earplug in an upright or lengthwise orientation. As a point of reference, disposable earplugs useful with the dispensers of the present disclosure can have a variety of different constructions (e.g., shapes, dimensions, materials, etc.), and the bores 60 are configured to accurately interface or handle a number of differently configured earplug designs, styles or formats. In more general terms, however, and with reference to FIG. 4A, a disposable earplug 70 defines a length L and a maximum outer width (or diameter) W. The length L is conventionally greater than the maximum width W such that FIG. 4A depicts the earplug 70 in an upright or lengthwise direction (i.e., a major axis defined by a shape of the earplug 70 is arranged vertically). Disposable earplugs useful with the present disclosure can have a variety of different shapes, such as the conical-like shape shown in FIG. 4A, or other shapes such as cylindrical or cylindrical-like, or a more complex shape. The present disclosure is not limited to any particular disposable earplug shape or size. With this in mind, FIGS. 4B and 4C illustrate that each of the bores 60 has a height H and minimum diameter D selected in accordance with the expected earplug length L and maximum width W, and in particular such that the earplug 70 can only be completely received and arranged within the bore 60 in the lengthwise direction. The bore diameter D is less than the expected length L of the earplug 70 so that the loaded earplug 70 occupies a majority of the height H, thus preventing a second earplug (not shown) from completely loading into the bore 60 "on top of" the already-loaded earplug 70 (and thus only a single earplug 70 will subsequently be dispensed from the bore 60). Stated otherwise, were the bore 60 sized so that the earplug 70 could be arranged horizontally within the bore 60 (or perpendicular to the height H of the bore 60), a second earplug could undesirably also fully load within the bore 60. However, the bore diameter D is at least slightly greater than the expected earplug maximum width W to permit the earplug 70 to readily enter or load within the bore 60 in the lengthwise orientation. In this regard, in some embodiments the dispensers of the present disclosure are configured to be equally useful with a number of different earplug shapes and sizes (e.g., eleven different disposable earplug formats), with the bore diameter D selected to be slightly greater than the largest earplug diameter from the earplug products intended to be used with the particular dispenser. The dimensional relationship between the bore 60 and the earplug 70 reflected in the views of FIGS. 4B and 4C (in which the earplug 70 occupies a significant portion of the bore height H and diameter D) is but one example. Dispensers and dispensing mechanisms of the present disclosure are equally useful with other earplug sizes, including those that are smaller than the earplug 70 illustrated. Thus, other earplugs may be shorter (and thus occupy less of the bore height H) and/or more narrow (and thus occupy less of the bore diameter D) as compared to the relative sizes of FIGS. 4B and 4C.

As identified in FIGS. 4B and 4C, each of the bores 60 is generated or circumscribed by a wall surface 80. While in theory it may be possible for the individual earplug 70 to reside within a corresponding one of the bores 60 without contacting the wall surface 80 of the bore 60, in actual practice, the earplug 70 will be in virtually constant contact with various regions of the wall surface 80. With this in mind, in some embodiments the wall surface 80 optionally incorporates one or more anti-bonding constructions or features that promote low friction interface with the disposable earplug 70. More particularly, the wall surface 80 is optionally configured to promote sliding interface with an outer surface of the earplug 70 that conventionally is at least somewhat tacky or sticky. The sliding interface can be provided by forming a macroscopic roughness at or on at least a portion of the wall surface 80. For example, in some embodiments the wall surface 80 forms or defines a plurality of longitudinal ribs 82. The ribs 82 collectively form a ribbed macrostructure, with circumferentially adjacent ones of the ribs 82 being separated by a groove 84. A radial height of each of the ribs 82 (and thus a depth of each of the grooves 84) can be on the order of at least 0.3 mm, although other dimensions (either greater or lesser) are also acceptable. The ribs 82 can be uniformly formed about a circumference of the wall surface 80, with a circumferential width of each of the grooves 84 being on the order of not less than 1 mm although other dimensions (either greater or lesser) are also acceptable. The ribs 82 can generally follow the intended drop direction of the earplug 70 (e.g., are substantially parallel (e.g., within 5% of a truly parallel relationship) with a center line of the bore 60 and thus with the longitudinal axis A (FIG. 3C)). Alternatively, the ribs 82 can be arranged at an angle relative to the bore center line, defining a slight spiral or twist or rifling in extension between opposing ends of the wall surface 80. Finally, while the ribs 82 have been illustrated as being formed or provided along an entirety of the wall surface 80 (e.g., extending between the platform 56 and an opposing, terminal end of the bore 60), in other embodiments the ribs 82 (or other earplug interface surface enhancing feature) can encompass only a portion of the wall surface 80.

In other embodiments, the ribs 82 are replaced by another form of macroscopic surface texturing or roughening (e.g., the wall surface 80 can be knurled), or formed by a series of bumps or rings or other shaped protrusions configured to provide a low friction interface with a disposable earplug in contact therewith. In yet other embodiments, the optional anti-bonding construction or feature provided with the wall surface 80 includes a coating or forming the wall surface 80 with a low surface energy material to reduce adhesive forces between the earplug 70 and the wall surface 80 (e.g., a low surface energy material is one that exhibits a tendency to repel, rather than attract, the stick surface present on some disposable earplugs). The low surface energy material can be any material naturally exhibiting low surface energy or can be a material incorporated into a material of the wall surface 80 (e.g., the hub 50, and thus the wall surface 80, can be a molded plastic, with the plastic material or resin including a low surface energy additive, such as a fluoropolymer (e.g., available from 3M Company of St. Paul, Minn. under the trade name 3M™ Dyneon™)).

The optional anti-bonding constructions or features in accordance with the present disclosure include any surface feature that lessens frictional interface with an earplug as compared to the frictional interface that would otherwise be present between the earplug and a bore wall surface that did not include the anti-bonding construction or feature. The anti-bonding construction or feature can be chemical in nature (e.g., low surface energy material or coating), mechanical in nature (e.g., macroscopic roughness such as ribs), or a combination of both. In yet other embodiments, the wall surface 80 can be smooth and formed of a material not having a low surface energy attribute.

Figure 3A:
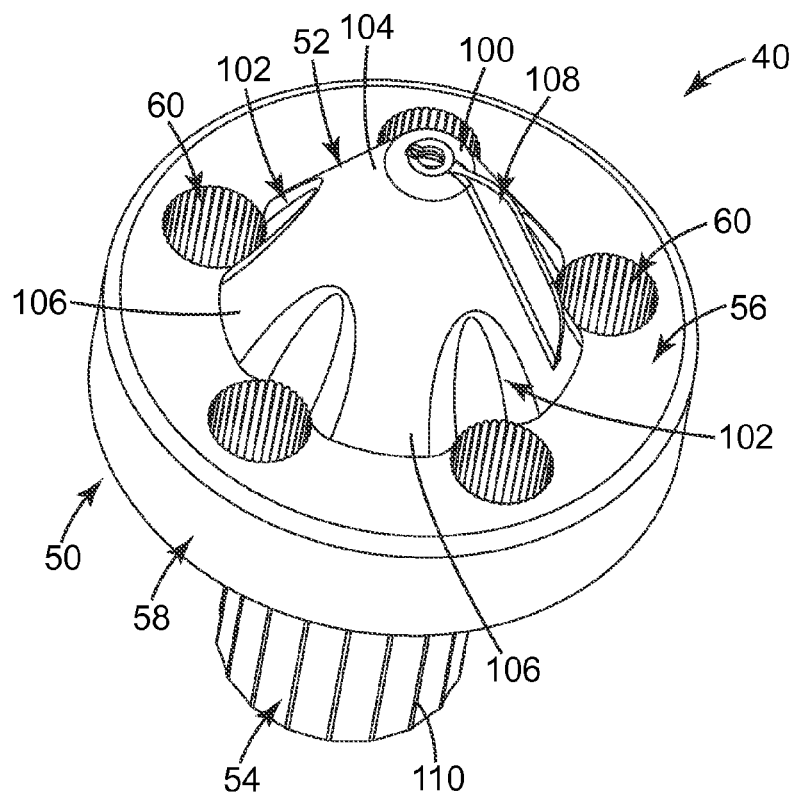
FIG. 3A is a perspective view of an index body portion of the dispensing mechanism of FIG. 2.
Figure 3B:
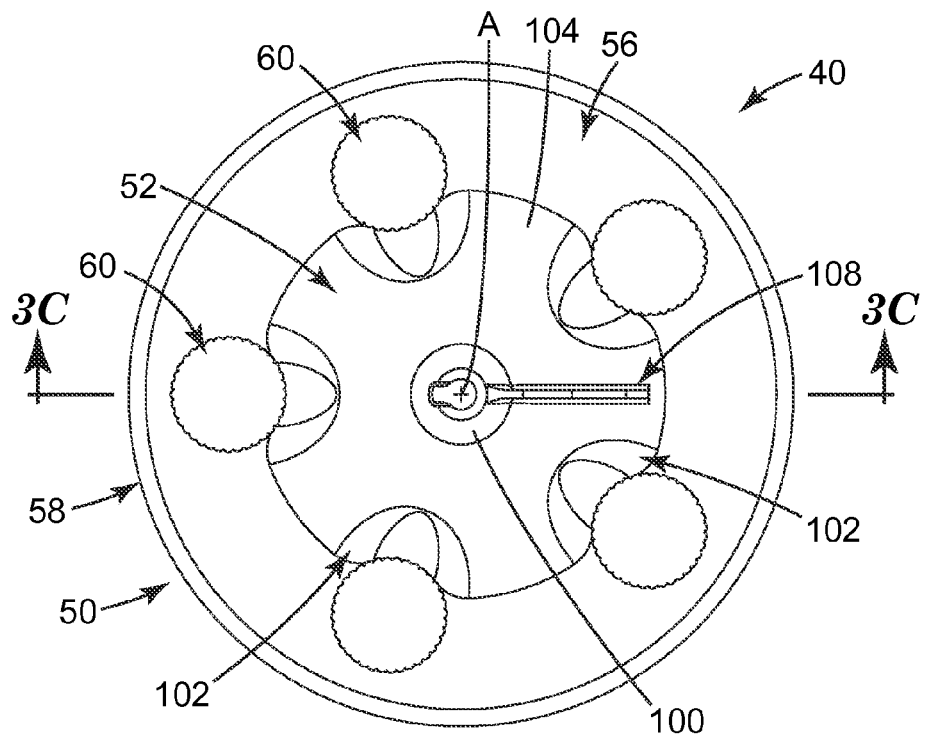
FIG. 3B is a top view of the index body of FIG. 3A.
Figure 3C:
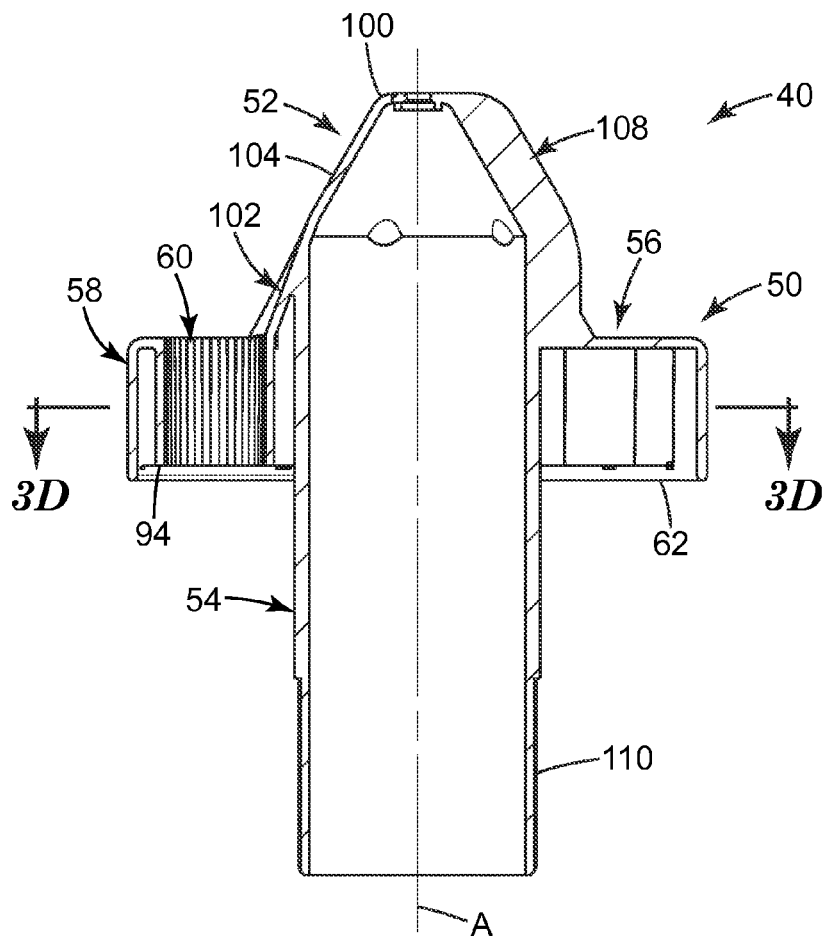
FIG. 3C is a cross-sectional view of the index body of FIG. 3B, taken along the line 3C-3C.
Figure 3D:
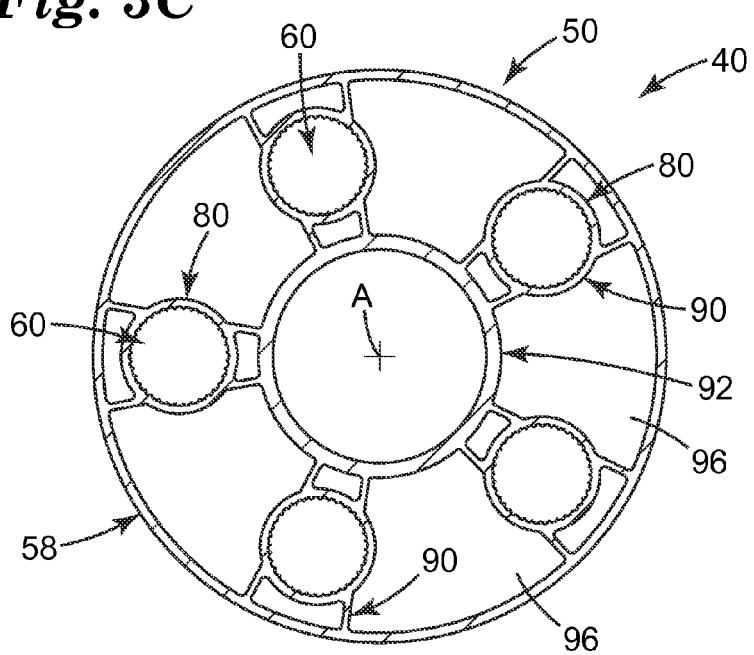
FIG. 3D is a cross-sectional view of the index body of FIG. 3C, taken along the line 3D-3D.

Returning to FIGS. 3A-3D, in some embodiments the wall surfaces 80 are each supported or defined by a bracket structure 90 (best seen in FIG. 3D) extending between the annular outer wall 58 and a central ring 92. The bracket structures 90 each support the corresponding wall surface 80 relative to the platform 56, with the corresponding bore 60 being open at a trailing end 94 (FIG. 3C) of the bracket structure 90. With this construction, an open region 96 (FIG. 3D) is generated between circumferentially adjacent ones of the bracket structures 90. Alternatively, the hub 50 can have a more solid construction. Finally, and as best shown in FIG. 3C, the open end 94 can optionally be located slightly above the lower major face 62 defined by the annular wall 58 for reasons made clear below.

The guide cone 52 projects upwardly from the platform 56 concentric with the longitudinal axis A and terminates at a leading end 100 opposite the platform 56. The guide cone 52 is generally conical in shape, tapering in outer diameter from the platform 56 to the leading end 100. A plurality of troughs 102 are optionally formed in an outer surface 104 of the guide cone 52, with each trough 102 being aligned with a corresponding one of the bores 60. A height of the guide cone 52 (i.e., longitudinal dimension between the platform 56 and the leading end 100) is greater than an expected length of the earplugs (not shown), with the troughs 102 being sized and shaped to guide a single earplug toward the corresponding bore 60 in the upright or lengthwise orientation described above. Apart from the troughs 102, however, an outer diameter of the guide cone 52 at the platform 56 can be greater than an interior diameter collectively defined by the bores 60. With this construction, the outer surface 104 forms a plurality of partitions 106 (FIGS. 3A and 3B), respective ones of which project into the spacing between circumferentially adjacent ones of the bores 60. Thus, at the platform 56, a radial distance between each of the partitions 106 and the annular outer wall 58 is less than a radial distance (i.e., radial or perpendicular relative to the longitudinal axis A) between each of the troughs 102 and the annular outer wall 58, with the decreased spacing possibly displacing un-loaded earplugs away from the platform 56 as described below.

Finally, the guide cone 52 can include a blade 108 projecting from the outer surface 104. The blade 108 is arranged radially relative to the longitudinal axis A, and is configured to promote mixing of earplugs (not shown) that are otherwise loosely arranged about the guide cone 52 with rotation of the index body 40.

The handle 54 projects downwardly relative to the hub 50 (i.e., in a direction opposite the guide cone 52), concentric about the longitudinal axis A. In some embodiments, the handle 54 can be considered to be an extension of the hub central ring 92. The handle 54 can define a contoured gripping surface 110 configured to promote interface with a user's fingers. Regardless of an exact construction, an outer diameter of the handle 54 is less than an interior diameter collectively defined by the plurality of bores 60. Stated otherwise, the bores 60 are located radially (i.e., perpendicular to the longitudinal axis A) beyond the handle 54 relative to the longitudinal axis A.

Figure 5A:
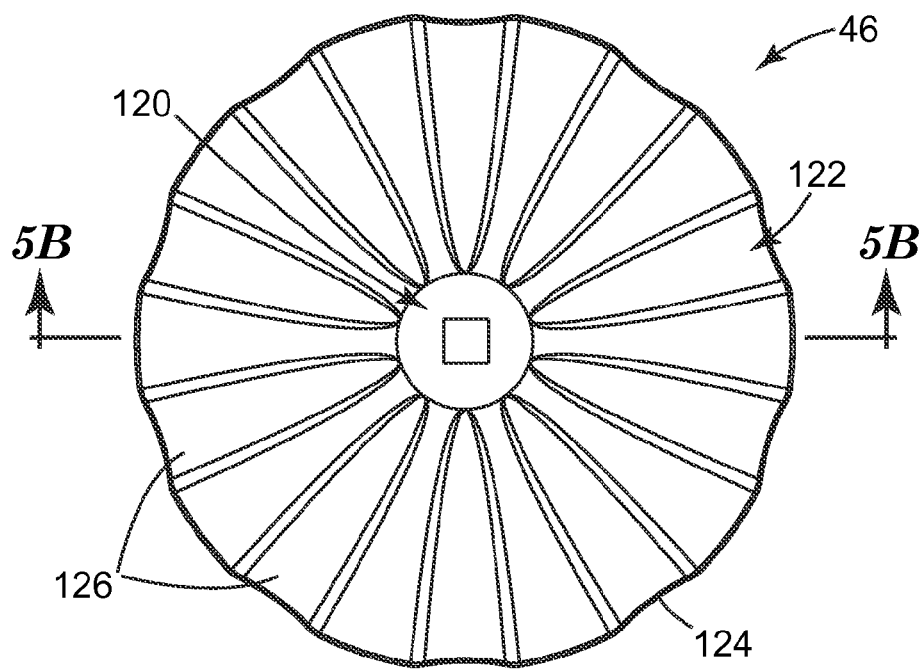
FIG. 5A is a top view of a shield useful with the dispensing mechanism of FIG. 2.
Figure 5B:
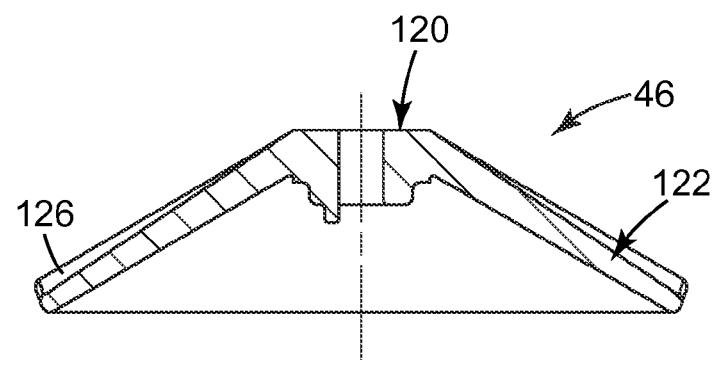
FIG. 5B is a cross-sectional view of the shield of FIG. 5A, taken along the line 5B-5B.

Returning to FIG. 2, where provided, the shield 46 is configured for assembly to the index body 40, and in other embodiments can be integrally formed with the index body 40. Regardless, and with reference to FIGS. 5A and 5B, the shield 46 includes or defines a base 120 and a shield wall 122. The shield wall 122 projects radially outwardly from the base 120 to a perimeter edge 124. Further, the shield wall 122 defines a conical-like shape, such that the shield 46 is akin to an umbrella. Contours 126 (e.g., grooves or slots) can be formed in an outer surface of the shield wall 122 for reasons made clear below. Regardless, an outer diameter of the shield 46 at the perimeter edge 124 is sized in accordance with corresponding features of the hub 50 (FIG. 3A).

Figure 6A:
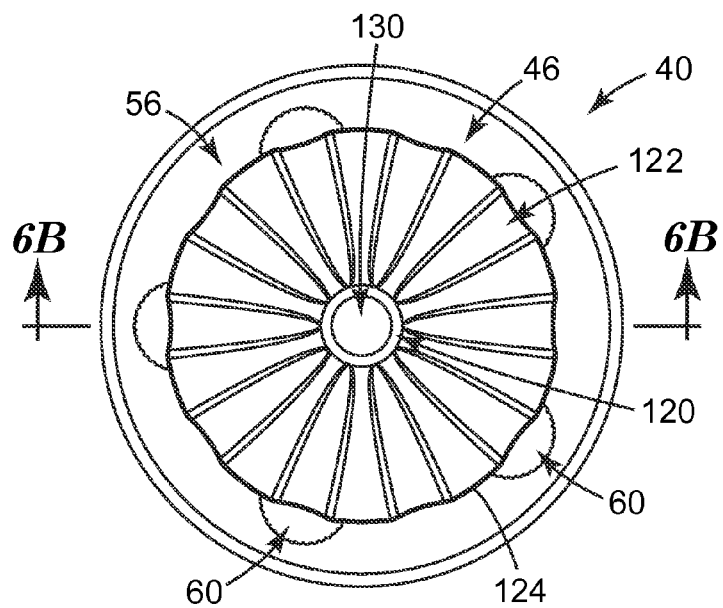
FIG. 6A is a top view of the index body of FIG. 3A assembled to the shield of FIG. 5A.
Figure 6B:
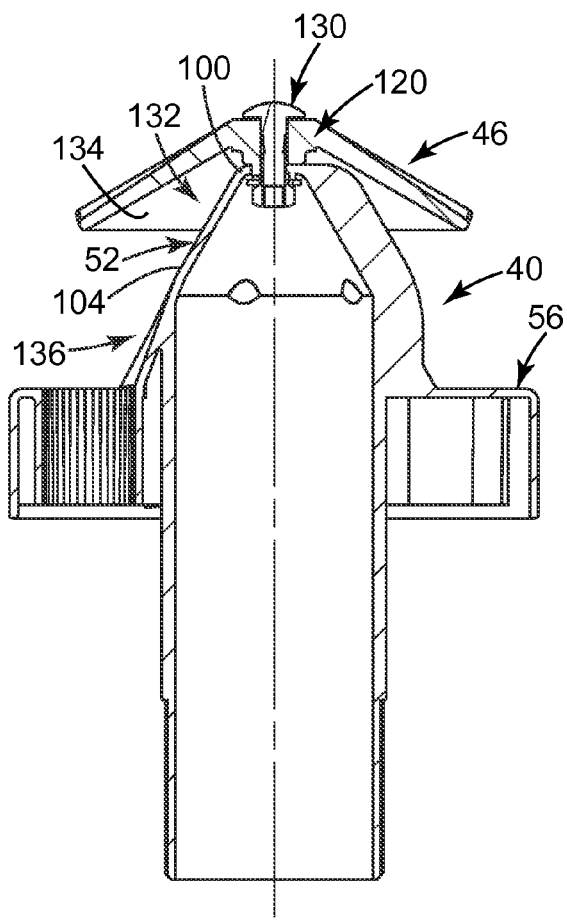
FIG. 6B is a cross-sectional view of the assembly of FIG. 6A, taken along the line 6B-6B.

More particularly, FIGS. 6A and 6B illustrate the shield 46 as assembled to the index body 40, for example via a dowel assembly 130. As shown, the base 120 is mounted above the leading end 100 of the guide cone 52, with the shield wall 122 extending outwardly as well as downwardly toward the platform 56. A taper angle of the shield wall 122 differs from that of the guide cone 52 such that the shield wall 122 is radially spaced from the outer surface 104 of the guide cone 52. As best shown in FIG. 6B, then, a spacing 132 is created between the outer surface 104 of the guide cone 52 and an underside 134 of the shield wall 122. With this arrangement, the perimeter edge 124 is radially spaced from the guide cone 52. The perimeter edge 124 is longitudinally spaced from the platform 56, thereby establishing a chamber 136 between the shield 46 and the platform 56. As described below, earplugs (not shown) can be loosely disposed within the chamber 136, with the shield 46 isolating the earplugs within the chamber 136 from other earplugs located above the shield 46. In this regard, and as best reflected in FIG. 6A, an outer diameter of the shield 46 at the perimeter edge 124 is greater than an interior diameter collectively defined by the bores 60. Stated otherwise, in the final assembled state of FIGS. 6A and 6B, the shield 46 projects over at least a portion of each of the bores 60, better ensuring that the chamber 136 includes at least a portion of each of the bores 60.

Returning to FIG. 2, the housing 42 is a generally ring-shaped structure, sized to rotatably receive the index body 40, and in particular the hub 50. For example, and with reference to FIGS. 7A-7C, the housing 42 includes or defines a sleeve 140, a guide wall 142, a capture ring 144, and a flange body 146. The sleeve 140 is cylindrical, concentrically arranged about a central axis C. The sleeve 140 extends between upper and lower ends 148, 150, and defines an interior surface 152 and an exterior surface 154. A diameter defined by the interior surface 152 (apart from the guide wall 142) corresponds with an outer diameter of the hub 50 (FIG. 3A), and in particular a diameter of the annular outer wall 58 (FIG. 3A). More particularly, the sleeve 140 defines an opening sized to coaxially receive the hub 50, with the annular outer wall 58 nesting against the interior surface 152 in a manner allowing the hub 50 to rotate relative to the sleeve 140.

The guide wall 142 projects radially inwardly (radial or perpendicular relative to the central axis C) from the upper end 148 of the sleeve 140. As best shown in FIG. 7C, the guide wall 142 terminates at an inner edge 160 that is longitudinally and radially offset from the upper end 148. Thus, a diameter of the inner edge 160 is less than that of the interior surface 152 at the sleeve 140. A guide surface 162 of the guide wall 142 can be substantially smooth and uniform in extension from the upper end 148 to the inner edge 160. In some embodiments, however, a barrier member 164 is defined along a portion of a circumference of the guide wall 142, formed as a radially inward (radial or perpendicular relative to the central axis C) projection or discontinuity in the otherwise uniform guide surface 162. As seen in FIG. 7B, the barrier member 164 is formed along only a portion of the circumference of the guide wall 142, and thus has an arc angle of less than 360 degrees, alternatively less than 90 degrees. In this regard, an arc length of the barrier member 164 corresponds with geometric features of the index body 40 (FIG. 2), as does a radius of the inner edge 160 at the guide surface 162 and the barrier member 164 as made clear below.

The capture ring 144 is coaxially disposed about the sleeve 140 adjacent the upper end 148. A slot 170 is defined between the capture ring 144 and the exterior surface 154 of the sleeve 140, and is sized to receive a neck (not shown) of the container 32 (FIG. 1A). In this regard, the housing 42 can include various features, such as locking tabs 172, which selectively capture the container neck within the slot 170.

Figure 7A:
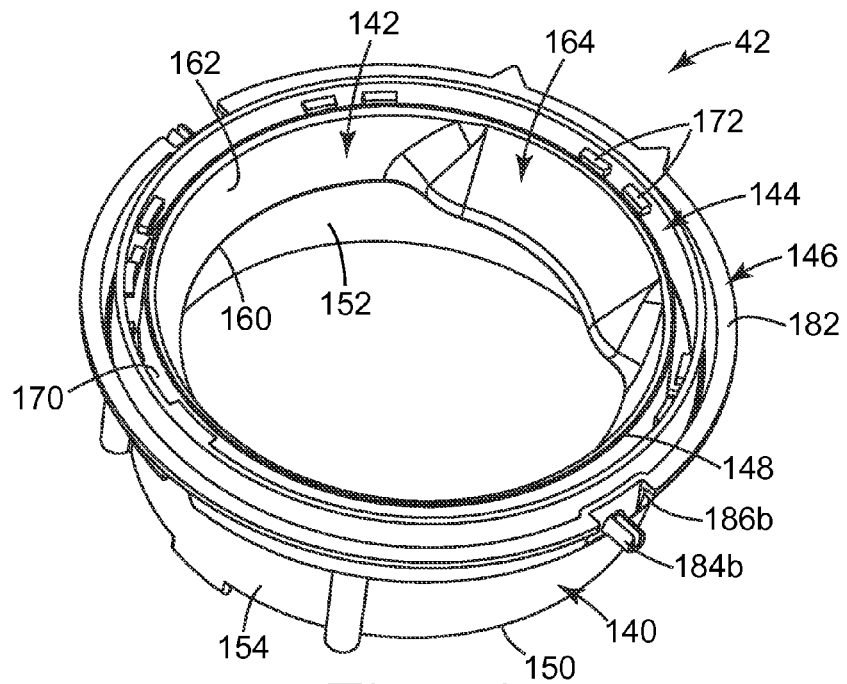
FIG. 7A is a perspective view of a housing useful with the dispensing mechanism of FIG. 2.
Figure 7B:
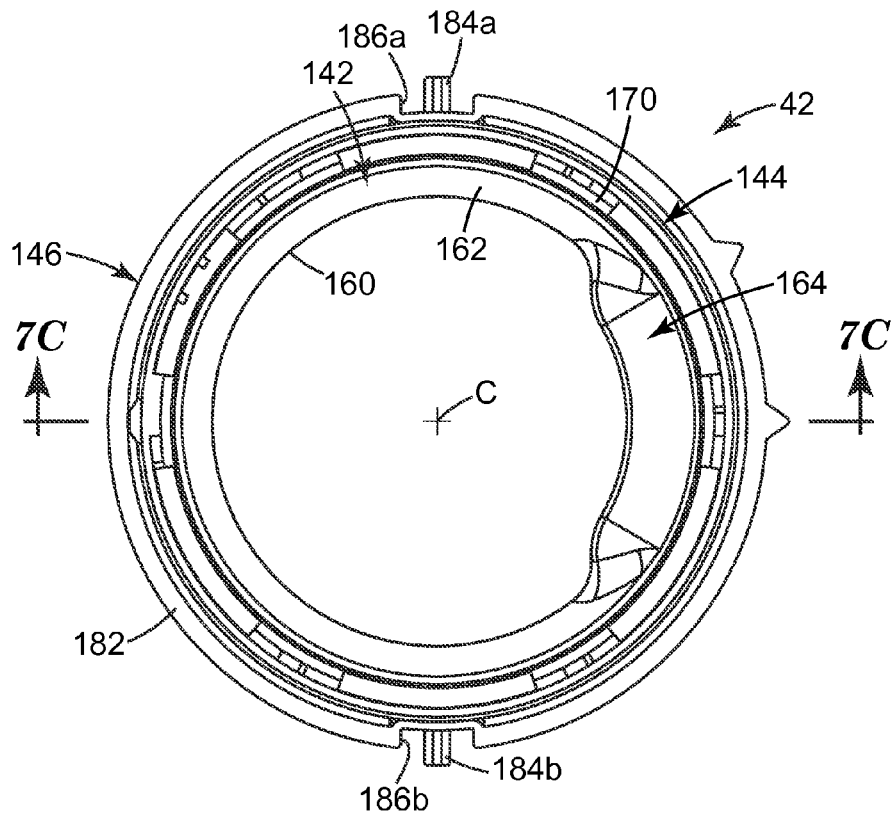
FIG. 7B is a top view of the housing of FIG. 7A.
Figure 7C:
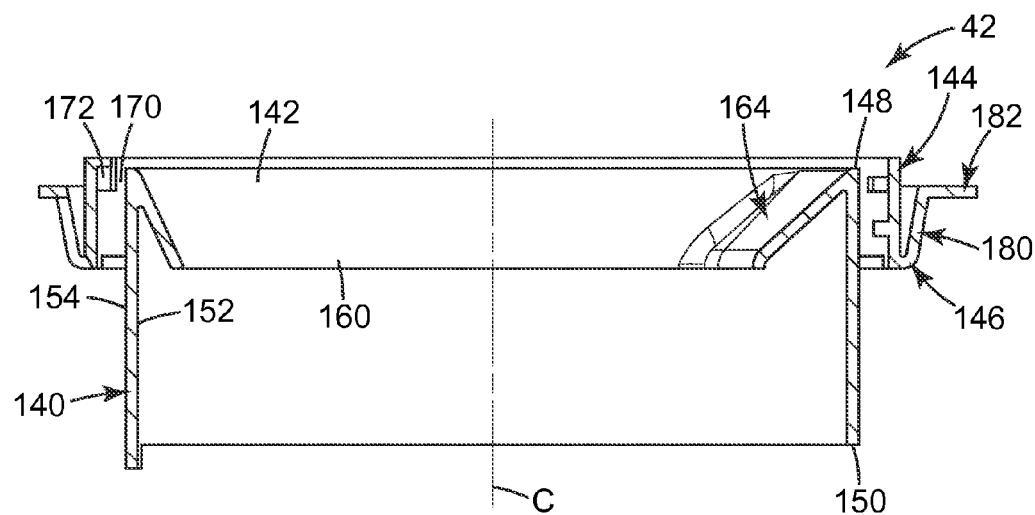
FIG. 7C is a cross-sectional view of the housing of FIG. 7B, taken along the line 7C-7C.
Figure 8A:
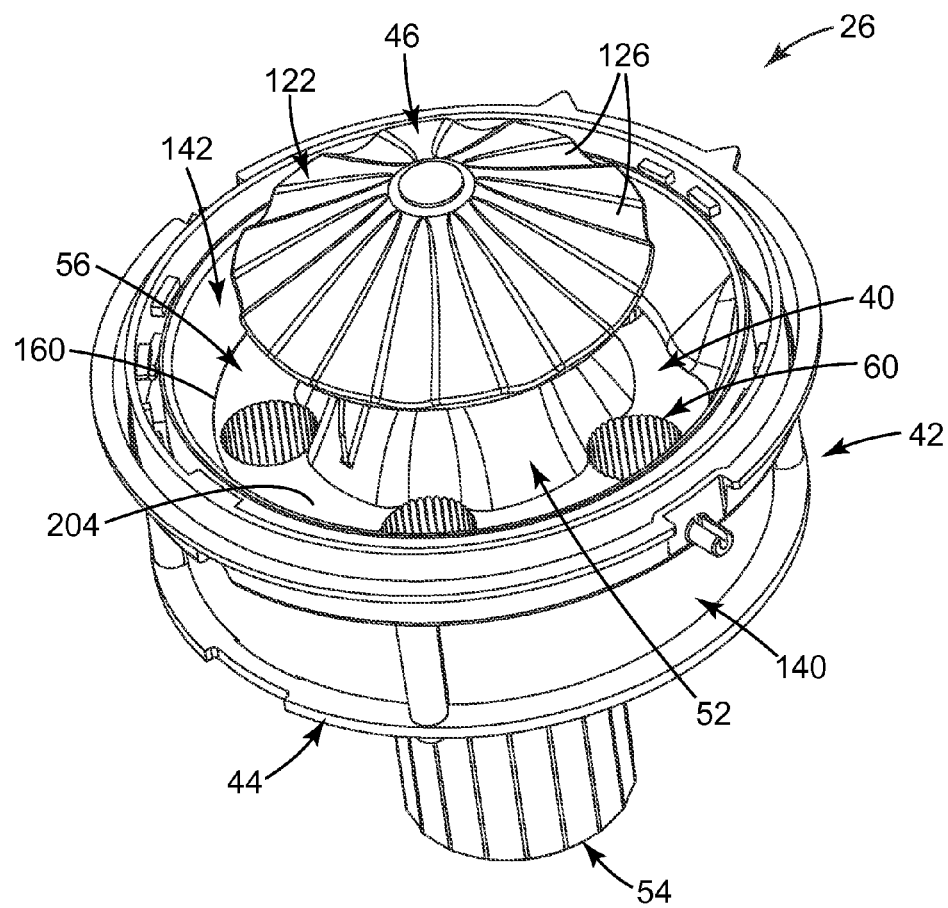
FIG. 8A is a perspective view of the dispensing mechanism of FIG. 2 upon final assembly.
Figure 8B:
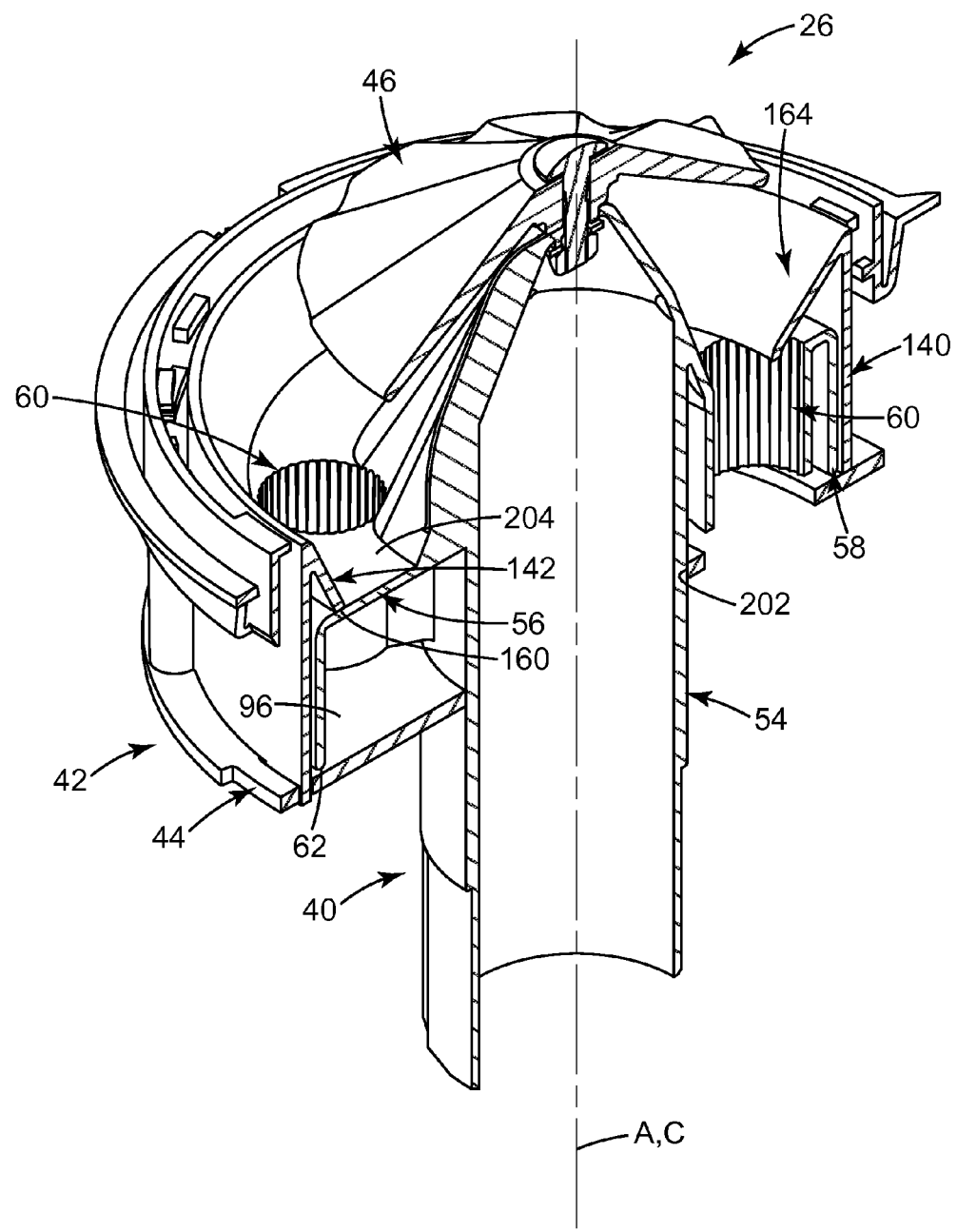
FIG. 8B is a perspective, cross-sectional view of the dispensing mechanism of FIG. 8A.
Figure 8C:
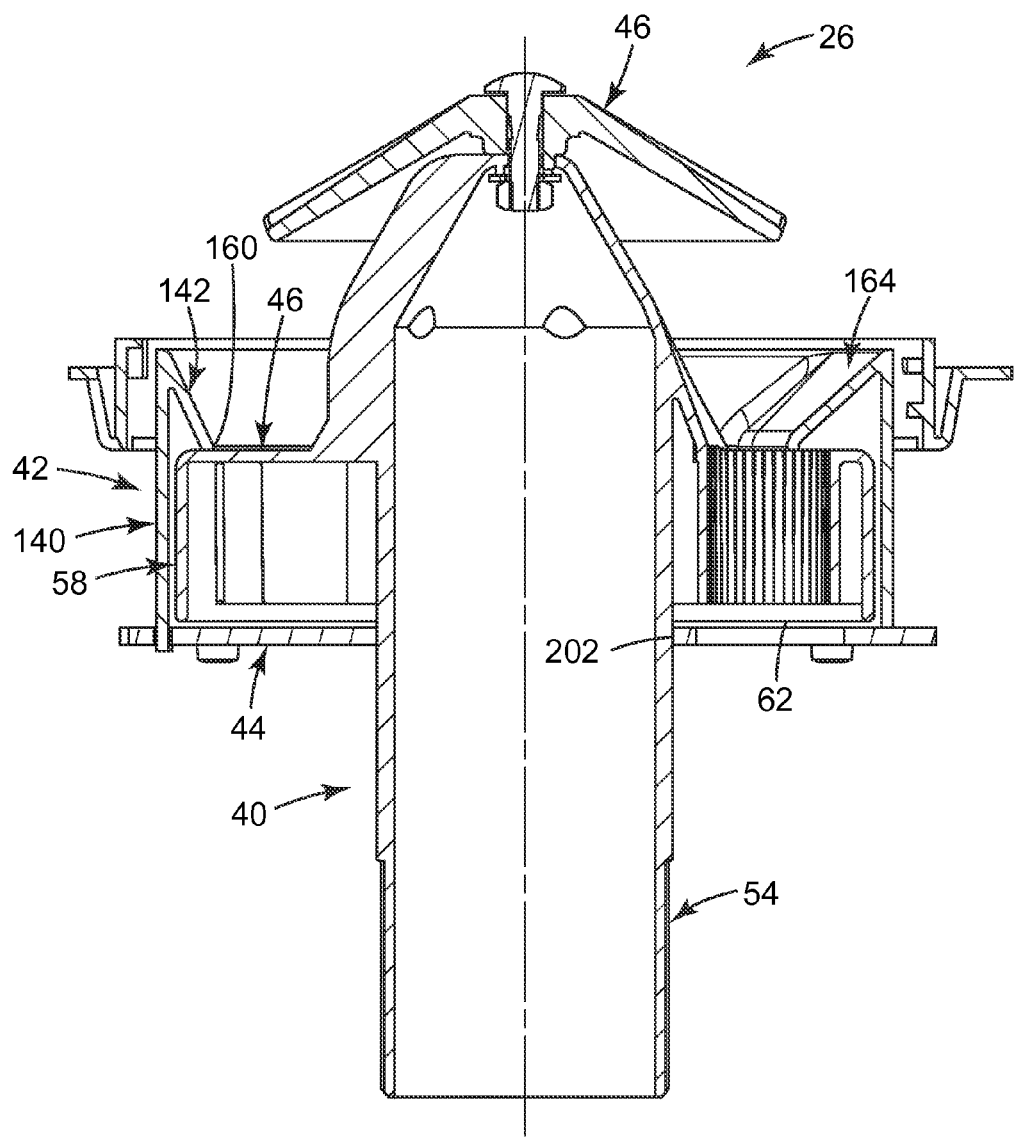
FIG. 8C is a longitudinal, cross-sectional view of the dispensing mechanism of FIG. 8A.
Figure 8D:
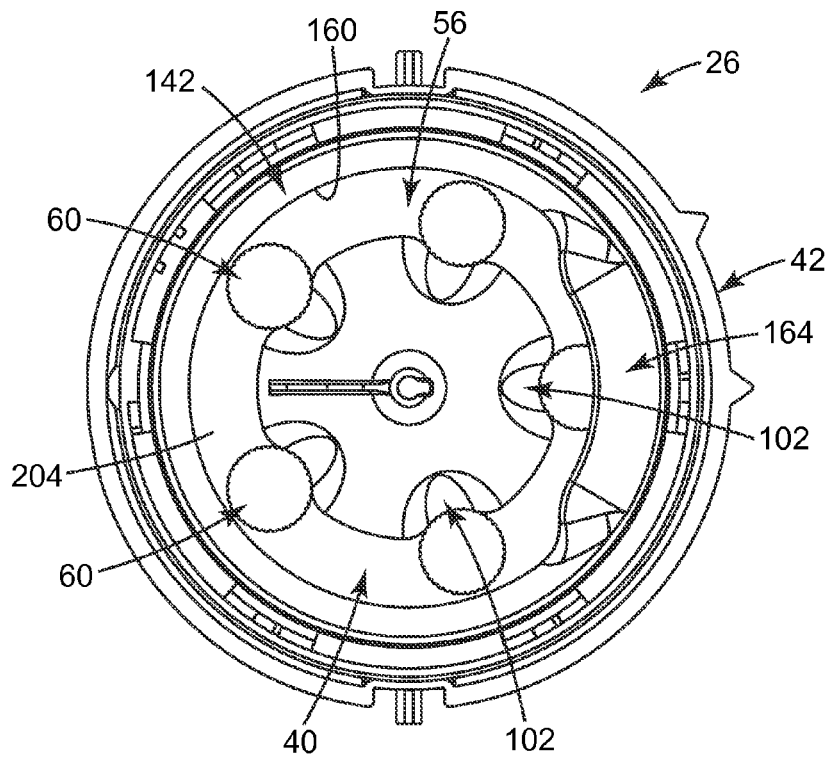
FIG. 8D is a top view of a portion of the dispensing mechanism of FIG. 8A.

With continued reference to FIGS. 7A-7C, the flange body 146 includes a shoulder 180 and a flange 182. The shoulder 180 is connected to and extends from the capture ring 144, with the flange 182 projecting radially outwardly from the shoulder 180. In general terms, the flange body 146 is sized and shaped in accordance with features associated with the frame 28 (FIG. 1A) such that the housing 42 can be mounted to the frame 28 via the flange body 146. In this regard, in some embodiments the housing 42 is desirably mounted to the frame 28 such that the housing 42 cannot rotate relative to the frame 28. Optional components useful in insuring this non-rotational coupling are described below. However, the flange body 146 can include or provide additional features that cooperate with the additional components, such as pins 184a, 184b arranged adjacent a corresponding notch 186a, 186b in the flange 182.

Returning to FIG. 2, the plate 44 is configured for fixed assembly to the housing 42, and defines a dispensing aperture 200. As described in greater detail below, operation of the dispensing mechanism 26 entails selective alignment of respective ones of the bores 60 with the dispensing aperture 200 for dispensement of an earplug (not shown) through the dispensing aperture 200. Thus, the dispensing aperture 200 has a size and shape generally corresponding with the size and shape of each of the bores 60. For example, in some embodiments, the dispensing aperture 200 is larger than the bores 60. However, a circumferential width of the dispensing aperture 200 is less than the arc length between two circumferentially adjacent bores 60 such that only a single one of the bores 60 is "within" the dispensing aperture 200 at any rotational position of the index body 40 relative to the plate 44.

The plate 44 can employ a variety of differing features that facilitate assembly as part of the dispensing mechanism 26. For example, in some embodiments, the plate 44 has a circular perimeter that generally corresponds with the shape of the housing 42, and forms a central hole 202 sized to coaxially receive the index body handle 54.

Final assembly of the dispensing mechanism 26 is shown in FIGS. 8A-8D. The index body 40 is coaxially disposed within the housing 42, with the hub annular wall 58 nesting within the sleeve 140. The plate 44 is assembled to the housing 42, for example with the handle 54 being rotatably received within the hole 202. The plate 44 is affixed to the housing 42, whereas the index body 40 is rotationally mounted to the housing 42. More particularly, the hub 50 is captured between the guide wall 142 of the housing 42 and the plate 44. The inner edge 160 of the guide wall 142 can contact or be slightly spaced from the platform 56, and the lower major face 62 of the annular outer wall 58 can contact or be slightly spaced from the plate 44. Regardless, an outer diameter of the hub 50 is slightly less than an inner diameter of the sleeve 140 such that the hub 50 can rotate relative to the sleeve 140. With this construction, then, the index body 40 is rotatable relative to the housing 42 and the plate 44 about the longitudinal axis A (that is otherwise aligned with the housing axis C). Finally, the shield 46 (where provided) is affixed to the index body 40 and rotates with rotation of the index body 40. In other embodiments, however, the shield 46 can be rotationally isolated from the index body 40.

The guide cone 52 and the guide wall 142 combine to create an annular channel 204 adjacent to the bores 60. As highlighted by the top view of FIG. 8D (in which the shield 46 is omitted for ease of explanation), the inner edge 160 of the guide wall 142 is located at the platform 56 immediately adjacent the radially outermost portion of the each of the bores 60 in some embodiments, but does not cover the bores 60 (apart from the barrier member 164). In other embodiments, the inner edge 160 can be spaced from the radially outermost portion of each of the bores 60. Radially inward extension of the barrier member 164 projects within an outer circumference collectively defined by the bores 60. The arc length of the barrier member 164 is greater than a diameter of each of the bores 60, with an arc angle of the barrier member 164 approximating a circumferential spacing between two circumferentially adjacent ones of the bores 60. With this construction, a portion of at least one of the bores 60 is located "under" the barrier member 164. Consistent with the above descriptions, a radial distance (i.e., in a direction perpendicular to the axes A, C) between the partitions 106 and the guide wall 142 (at the platform 56) is less than a radial distance between the troughs 102 and the guide wall 142.

Figure 9A:
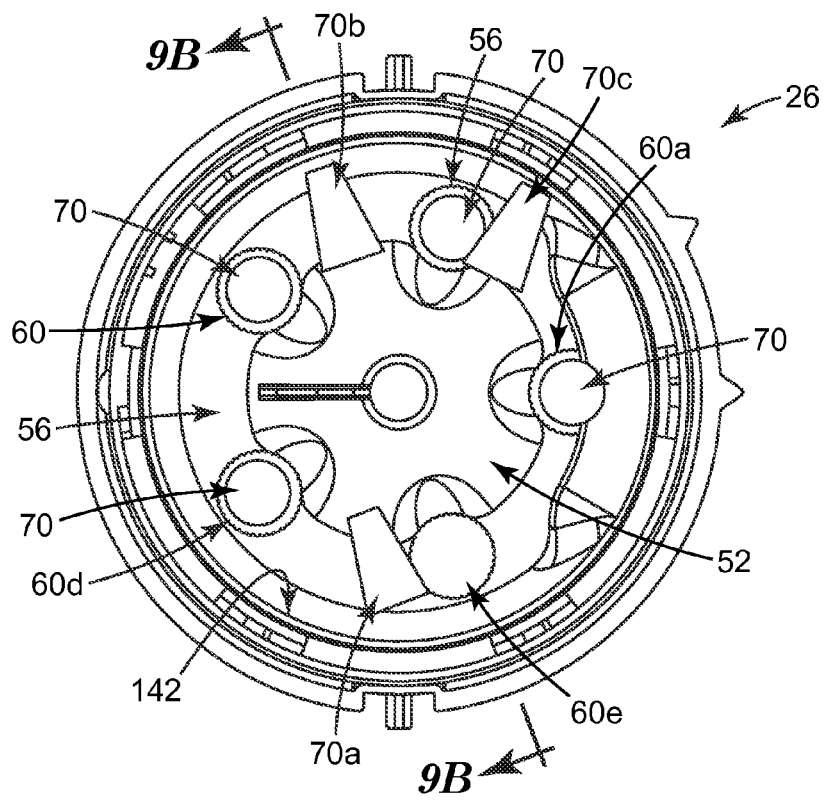
FIGS. 9A-9F illustrate operation of the dispensing mechanism of FIG. 8A in handling and dispensing disposable earplugs.
Figure 9B:
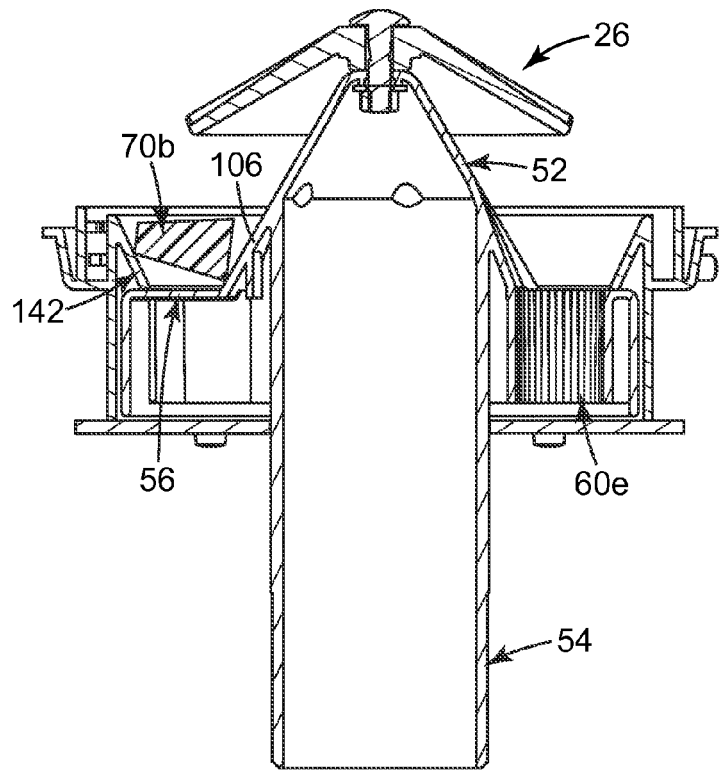

Operation of the dispensing mechanism 26 in handling and dispensing disposable earplugs 70 is generally reflected in FIGS. 9A-9F. For ease of illustration and understanding, the shield 46 is removed from the view of FIG. 9A. In the operational state of FIG. 9A, each of the first-fourth bores 60a-60d is loaded with an earplug 70, while the fifth bore 60e is empty. Several additional earplugs 70a-70c are loosely or randomly arranged in a vicinity of the platform 56. It will be understood that un-loaded earplugs will naturally and randomly assume virtually any orientation, and any un-loaded earplugs proximate the dispensing assembly 26 will randomly contact the dispensing mechanism 26 at any available surface such that the arrangements of FIG. 9A are merely one example. In some embodiments, a spacing between and geometry of the guide cone 52 and the guide wall 142 encourages at least some of the un-loaded earplugs 70a-70c slightly away from the platform 56 and into an orientation conducive to subsequent self-loading into an open bore 60. For example, FIG. 9B illustrates one possible, naturally occurring orientation of the second un-loaded earplug 70b. With cross-reference between FIGS. 9A and 9B, a radial distance between the partition 106 (of the guide cone 52) and the guide wall 142 is less than a length of the earplug 70b such that when arranged in the orientation of FIGS. 9A and 9B, the earplug 70b is lifted slightly above the platform 56. Further, the opposing taper angles of the guide cone 52 and the guide wall 142 tilts the earplug 70b (i.e., a centerline of the earplug 70b is non-parallel with the plane of the platform 56), with this tilted orientation being conducive to the earplug 70b self-loading within an open one of the bores 60 once aligned as described below. It will be understood that the location and orientation of the second earplug 70b in FIGS. 9A and 9B is only one possibility, and in many instances, un-loaded earplugs can and will be in contact with the platform 56. Further, other disposable earplugs useful with the present disclosure can have a shorter length and thus may not span across the guide cone 52 and the guide wall 142 even in the orientation of FIG. 9B. By optionally lifting at least some of the un-loaded earplugs 70a-70c away from the platform 56, the likelihood of a stray, un-loaded earplug becoming lodged within gaps between moving parts of the dispensing mechanism 26 is reduced, thus reducing malfunctions or "jamming" of the dispensing mechanism 26.

Figure 9C:
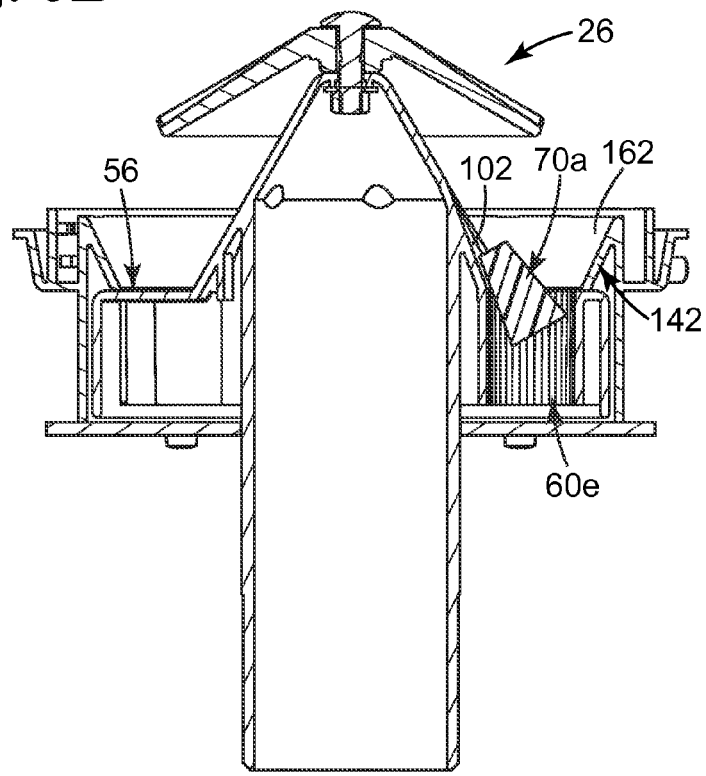
Figure 9D:
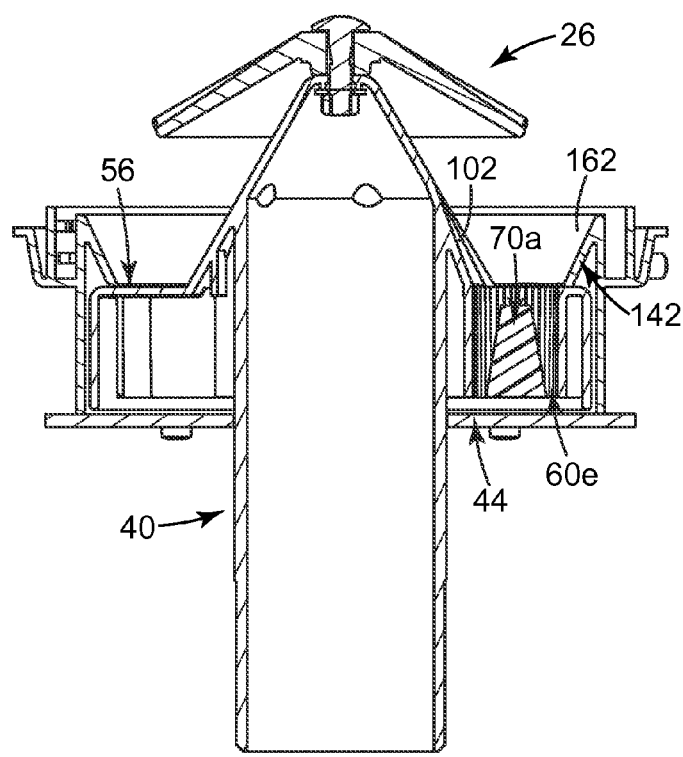

With rotation of the index body 40 (e.g., user-applied rotational force at the handle 54) relative to the housing 42 (e.g., clockwise relative to orientation of FIG. 9A) and/or due to gravity, the first un-loaded earplug 70a becomes aligned with and self-loads into the fifth bore 60e as shown in FIGS. 9C and 9D. In this regard, a radial distance between the corresponding trough 102 and the guide wall 142 tapers in a direction of the platform 56, allowing the earplug 70a to drop (due to gravity) toward the bore 60e. Further, the guide surface 162 of the guide wall 142 and the trough 102 corresponding with the fifth bore 60e assist in guiding the earplug 70a to slide directly into the bore 60e in an upright or lengthwise manner. The guide wall 142 and the trough 102 encourage the individual earplug 70a to readily drop into the open bore 60e, and as the earplug 70a drops or slides along either the guide surface 162 or the trough 102 (or both), the earplug 70a is naturally oriented lengthwise. Once inside the bore 60e (FIG. 9D), the earplug 70a can rest on the plate 44, sliding along a surface of the plate 44 as the index body 40 is rotated.

Figure 9E:
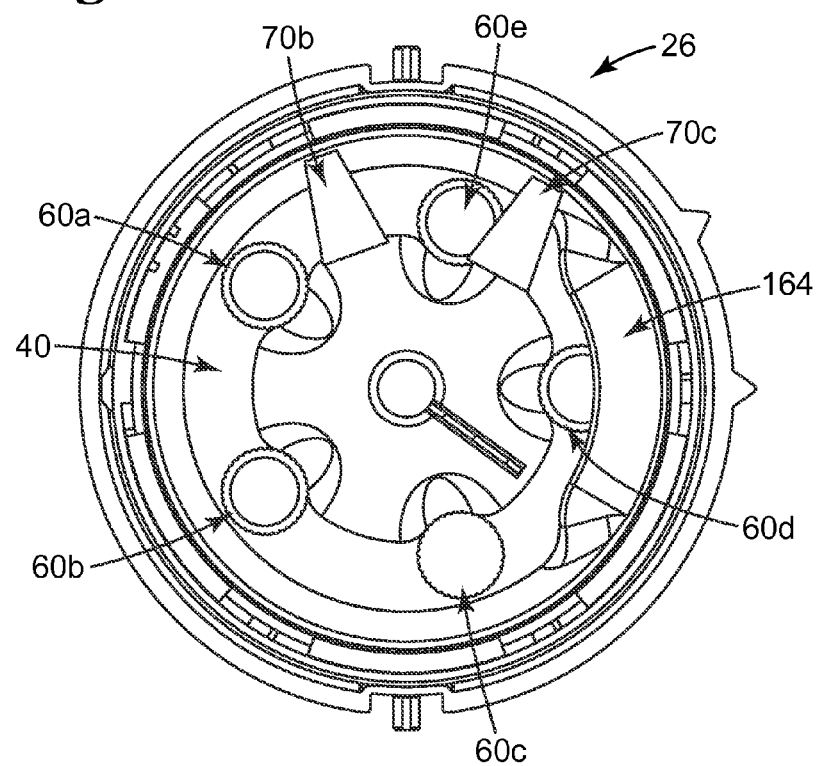
Figure 9F:
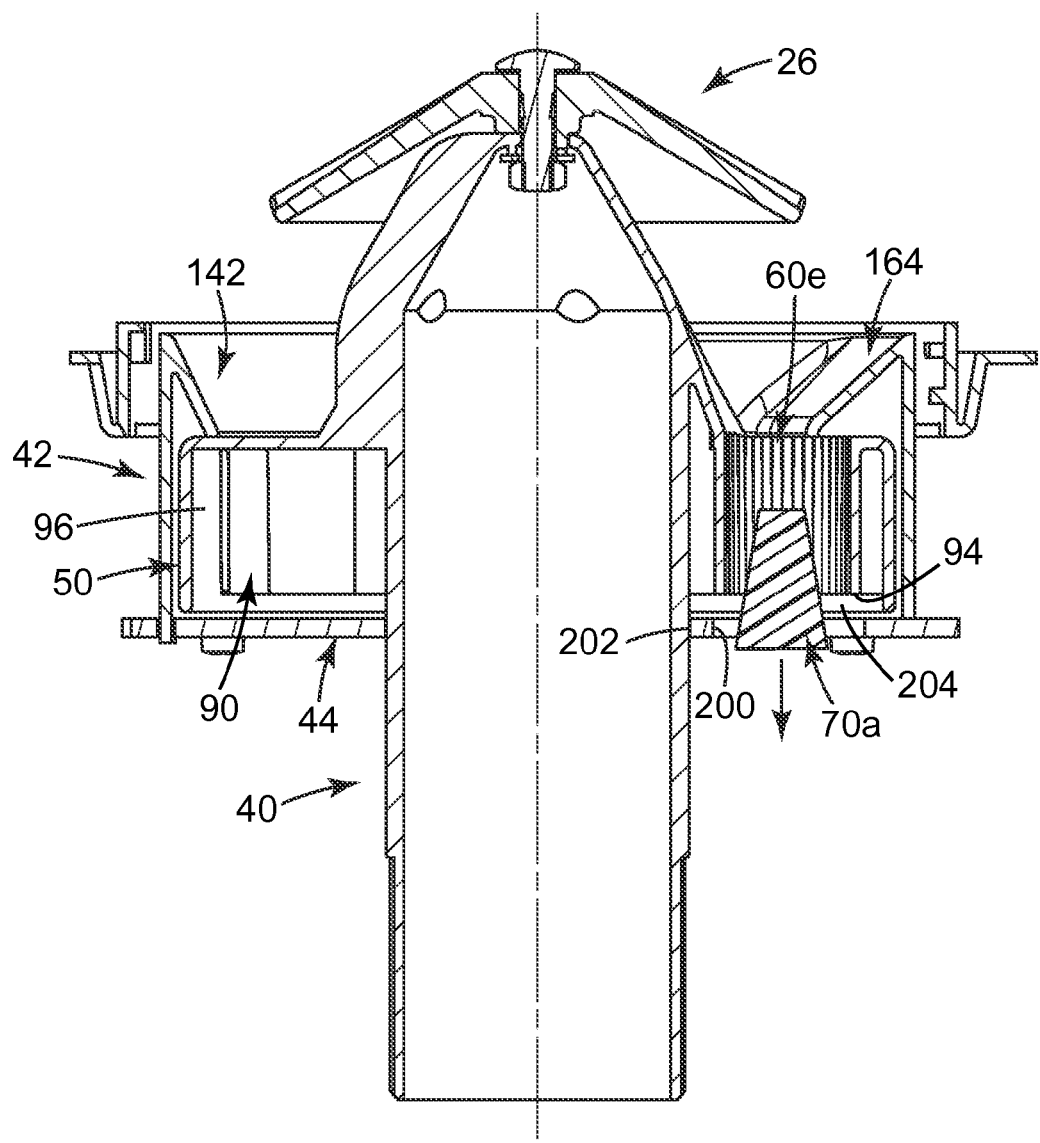

With reference to FIG. 9E, as the index body 40 is further rotated (e.g., clockwise direction relative to FIGS. 9A and 9E), the now-loaded fifth bore 60e is moved proximate the barrier member 164, and then passes under the barrier member 164. To the extent any un-loaded earplugs 70 (for example the third unloaded earplug 70c identified in FIG. 9E) is in a vicinity of the fifth bore 60e, the barrier member 164 ejects or clears the un-loaded earplugs 70 away from the fifth bore 60e as the fifth bore 60e is directed under the barrier member 164. Once the index body 40 has been rotated so as to align the fifth bore 60e with the dispensing aperture 200, the earplug 70a is released from the fifth bore 60e and falls through the dispensing aperture 200 due to gravity as shown in FIG. 9F (it being noted that the plate 44 is affixed to the housing 42 such that the dispensing aperture 200 remains stationary relative to the barrier member 164 during rotation of the index body 40). With further, continued rotation of the index body 40, a new earplug 70 will self-load into the now-open fifth bore 60e (as the fifth bore 60e progresses beyond the barrier member 164) for subsequent dispensement as described above.

As evidenced by the above explanations, the dispensing mechanism 26 incorporates a number of novel features that promote accurate and consistent loading and dispensing of the earplugs 70 on an individual or singular basis. For example, the wall surface texturing (e.g., the ribs 82 of FIGS. 4B and 4C) provided with the bores 60 promotes sliding of the earplugs 70 into and then from the bores 60 even under circumstances where the earplugs 70 are sticky or tacky. Further, the guide wall 142 consistently encourages the earplugs 70 to drop into any open bore 60 in the upright or lengthwise orientation.

As a point of reference, FIG. 9F illustrates an optional, small longitudinal gap 204 between the trailing end 94 of the bore 60e and the plate 44. In some instances, it may be possible for the earplug 70a to become lodged between the trailing end 94 and the plate 44 (and fail to drop through the dispensing aperture 200) due to the compressible nature of the earplug 70a, for example if the index body 40 is rapidly rotated. The dispensing mechanism 26 optionally includes features intended to prevent the dispensing mechanism 26 from jamming under these circumstances. For example, and as described above with respect to FIG. 3D, the hub 50 forms the bores 60 via the bracket structures 90, with the bracket structures 90 being spaced from one another by the open regions 96. If the earplug 70a becomes stuck between the trailing end 94 and the plate 44, the earplug 70a will slip between the corresponding bracket structure 90 and the plate 44 (at the gap 204) to the adjacent open region 96 with further rotation of the index body 40. It will be understood that while one of the open regions 96 is identified in FIG. 9F (and in FIG. 8B), the open region immediately adjacent the fifth bore 60e is not visible in the view of FIG. 9F. When the earplug 70a reaches the open region 96, it will decompress/expand. As the open region 96 is subsequently brought into alignment with the dispensing aperture 200, the earplug 70a will drop through.

Figure 10A:
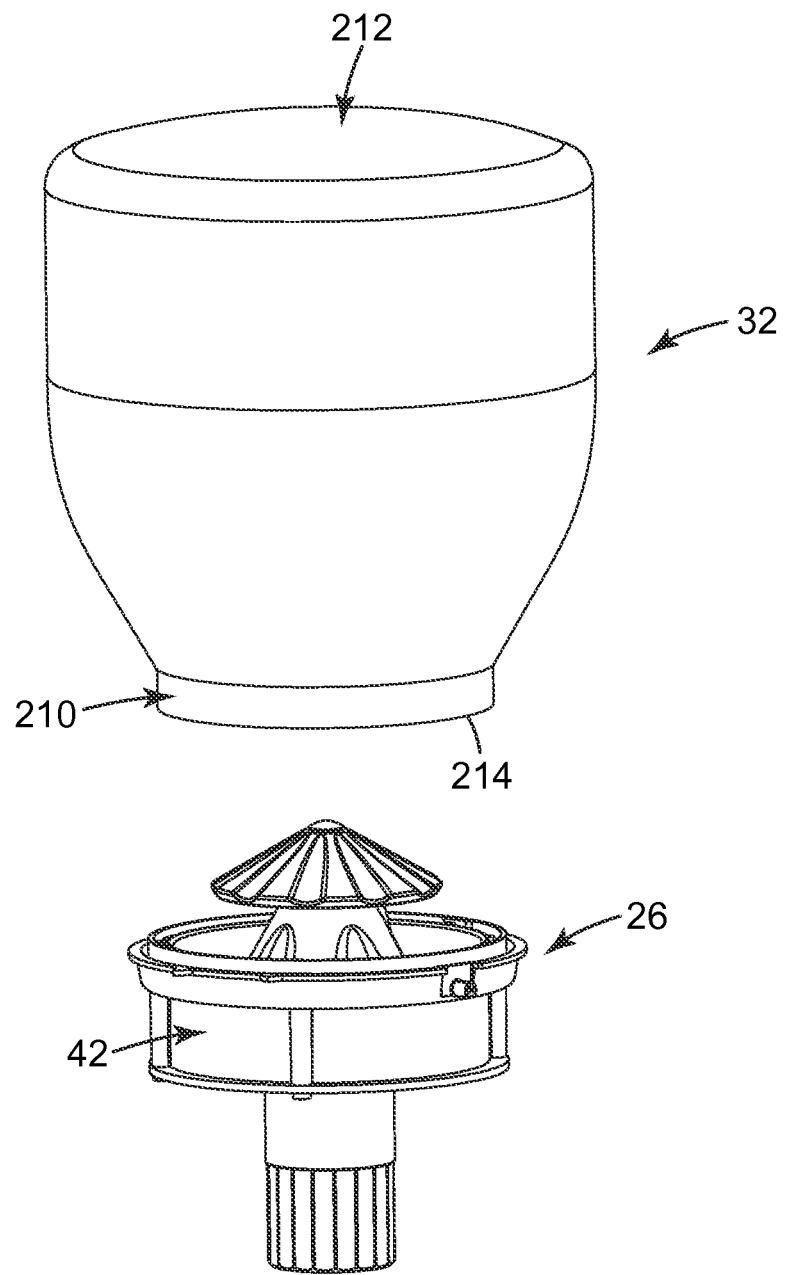
FIG. 10A is a perspective, exploded view of a portion of the dispenser of FIG. 1A, including the dispensing mechanism of FIG. 8A and a container.

While FIGS. 9A-9F reflect operation of the dispensing mechanism 26 relative to a few earplugs, it will be understood that the dispensing mechanisms of the present disclosure are useful in handling and dispensing individual earplugs from a bulk supply. For example, and as alluded to above, the housing 42 is configured for selective assembly to a container of earplugs. With this in mind, FIG. 10A illustrates one embodiment of the container 32 relative to the dispensing mechanism 26. The container 32 can assume a wide variety of forms, and can be sized to contain any number of earplugs (not shown). Thus, the present disclosure is in no way limited to the container 32 as shown. In general terms, the container 32 provides an enclosed volume within which the supply of earplugs is retained. The container 32 forms a neck 210 opposite a floor 212. The neck 210 terminates at an open end 214 (referenced generally) that is open to the internal volume. As a point of reference, a cover (not shown) can be provided with the container 32 for temporarily closing the open end 214. Thus, for example, prior to mounting to the dispensing mechanism 26, the container 32 can be closed and stored in an upright orientation via the floor 212. Regardless, a size and shape of the neck 210 corresponds with geometric features provided with the housing 42 in a manner promoting releasable mounting of the container 32 to the dispensing mechanism 26.

Figure 10B:
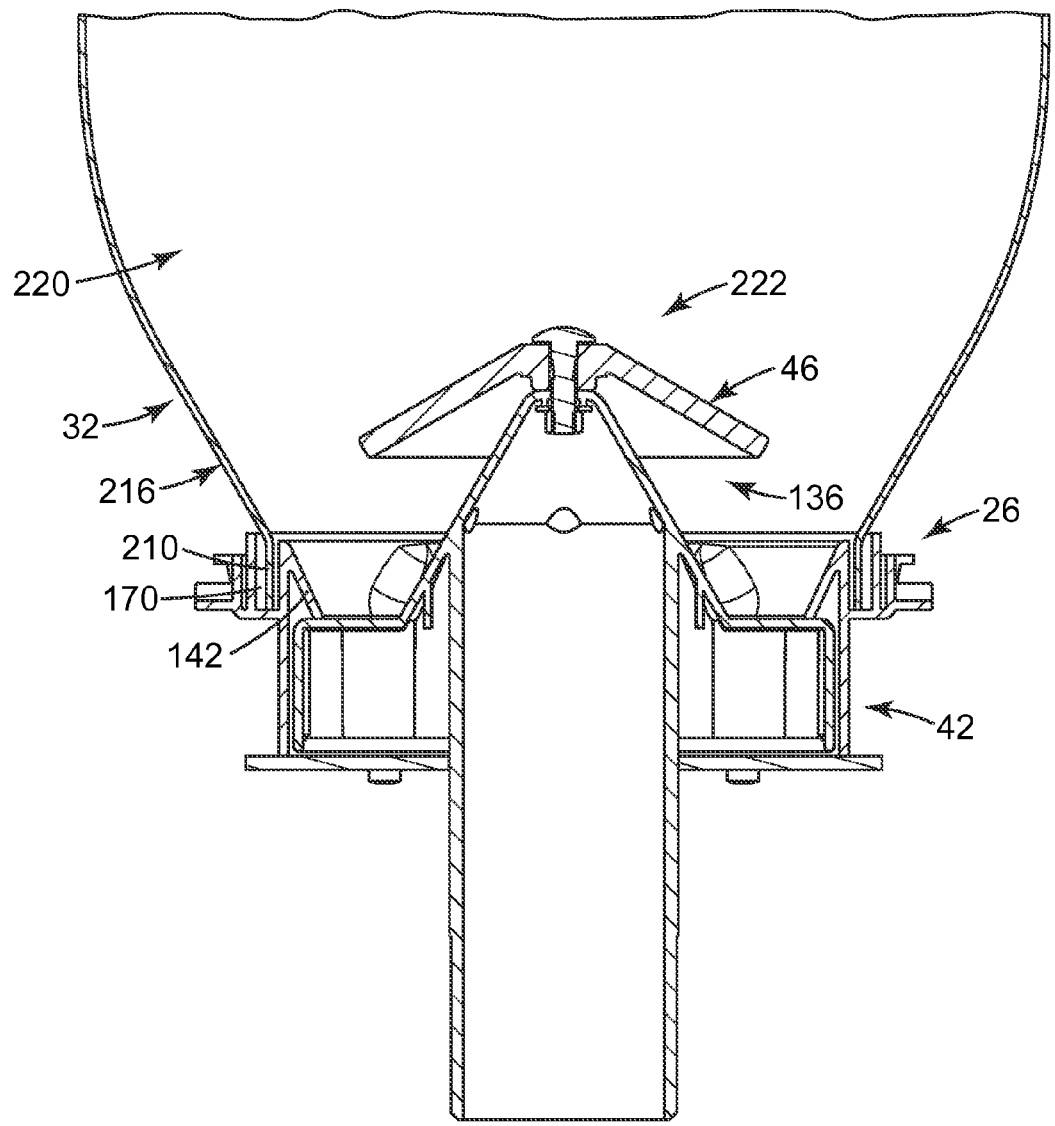
FIG. 10B is a cross-sectional view of a portion of the container and dispensing mechanism of FIG. 10A upon final assembly.

More particularly, and with reference to FIG. 10B, releasable assembly of the container 32 to the dispensing mechanism 26 includes insertion of the neck 210 into the slot 170 provided with the housing 42. A more robust connection between the container 32 and the dispensing mechanism 26 can be achieved via the optional locking tabs 172 (FIG. 7A) and/or other components. Regardless, a size and shape of the shield 46 is such that the neck 210 is easily introduced over the shield 46 and into engagement with the housing 42. In some embodiments, a size and shape of the neck 210 corresponds with a shape and spatial location of the guide wall 142 such that upon final assembly, a tapering region 216 of the container 32 is generally aligned with the angular orientation of the guide wall 142 such that earplugs (not shown) within the container 32 naturally flow toward and along the guide wall 142.

Figure 10C:
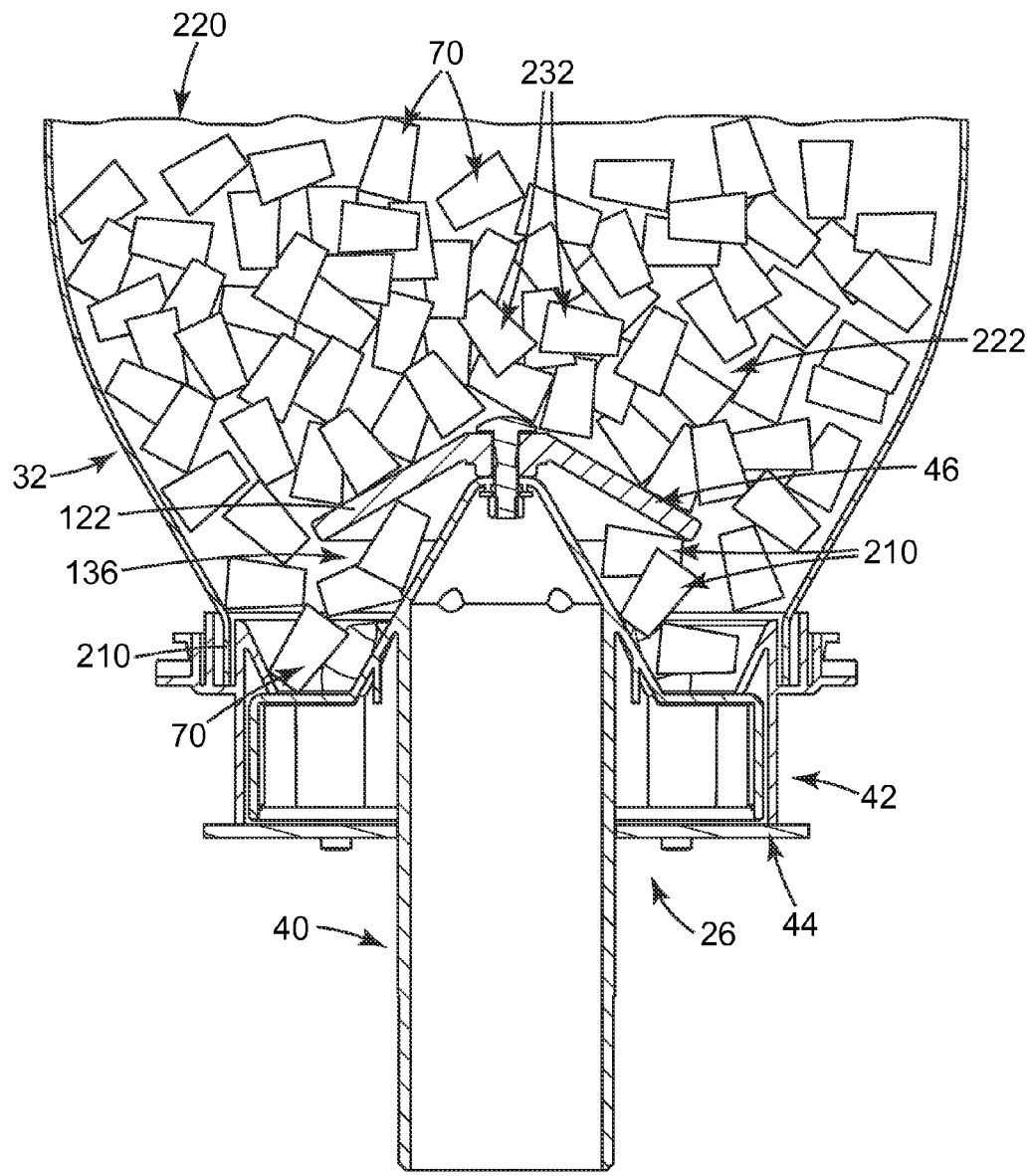
FIG. 10C is a cross-sectional view of the assembly of FIG. 11B and loaded with disposable earplugs.

Upon assembly of the container 32 to the dispensing mechanism 26, an effective storage volume 220 is collectively defined by the container 32 and the dispensing mechanism 26. The effective storage volume 220 includes an open volume of the container 32 and regions of the dispensing mechanism 26 above (relative to the orientation of FIG. 10B) the platform 56. With this in mind, the shield 46, where provided, divides the effective storage volume 220 into two chambers. The first chamber 136, as described above, is established between the shield 46 and the platform 56. A second chamber 222 is established above the shield 46 (relative to the orientation of FIG. 10B). When the effective storage volume 220 is relatively full of the disposable earplugs 70 as shown in FIG. 10C, a first grouping 230 (referenced generally) of the earplugs 70 will naturally reside or accumulate within the first chamber 136, and a second grouping 232 (referenced generally) of the earplugs 70 will naturally reside or accumulate within the second chamber 222. That is to say, due to gravity, some of the earplugs 70 initially within just the container 32 will fall into the first chamber 136 as the container 32 is mounted onto the dispensing mechanism 26 (or, with an alternative mounting technique in which the container 32 is oriented with the neck 210 facing upwards and the dispensing mechanism 26 is placed on to the neck 210, some of the earplugs 70 within the container 32 will drop into the first chamber 136 as the assembled dispensing mechanism 26/container 32 is then rotated to the orientation of FIG. 10C).

As individual ones of the earplugs 70 of the first grouping 230 are incrementally dispensed from the first chamber 136 with operation of the dispensing mechanism 26 (as described above), various ones of the earplugs 70 of the second grouping 232 will naturally move from the second chamber 222 into the first chamber 136 due to gravity. However, the shield 46 effectively prevents a collective weight of the second grouping 232 from acting upon the first grouping 230 within the first chamber 136. As a result, the earplugs 70 within the first chamber 136 are more loosely maintained relative to one another, and thus can more easily be separated from one another (with rotation of the index body 40) and become guided or loaded into individual ones of the bores 60 (FIG. 8A) as described above. Further, the contoured surface 126 (FIG. 8A) of the shield wall 122 promotes mixing of the earplugs 70 in contact therewith during rotation of the index body 40 (as does the blade 108).

Figure 11A:
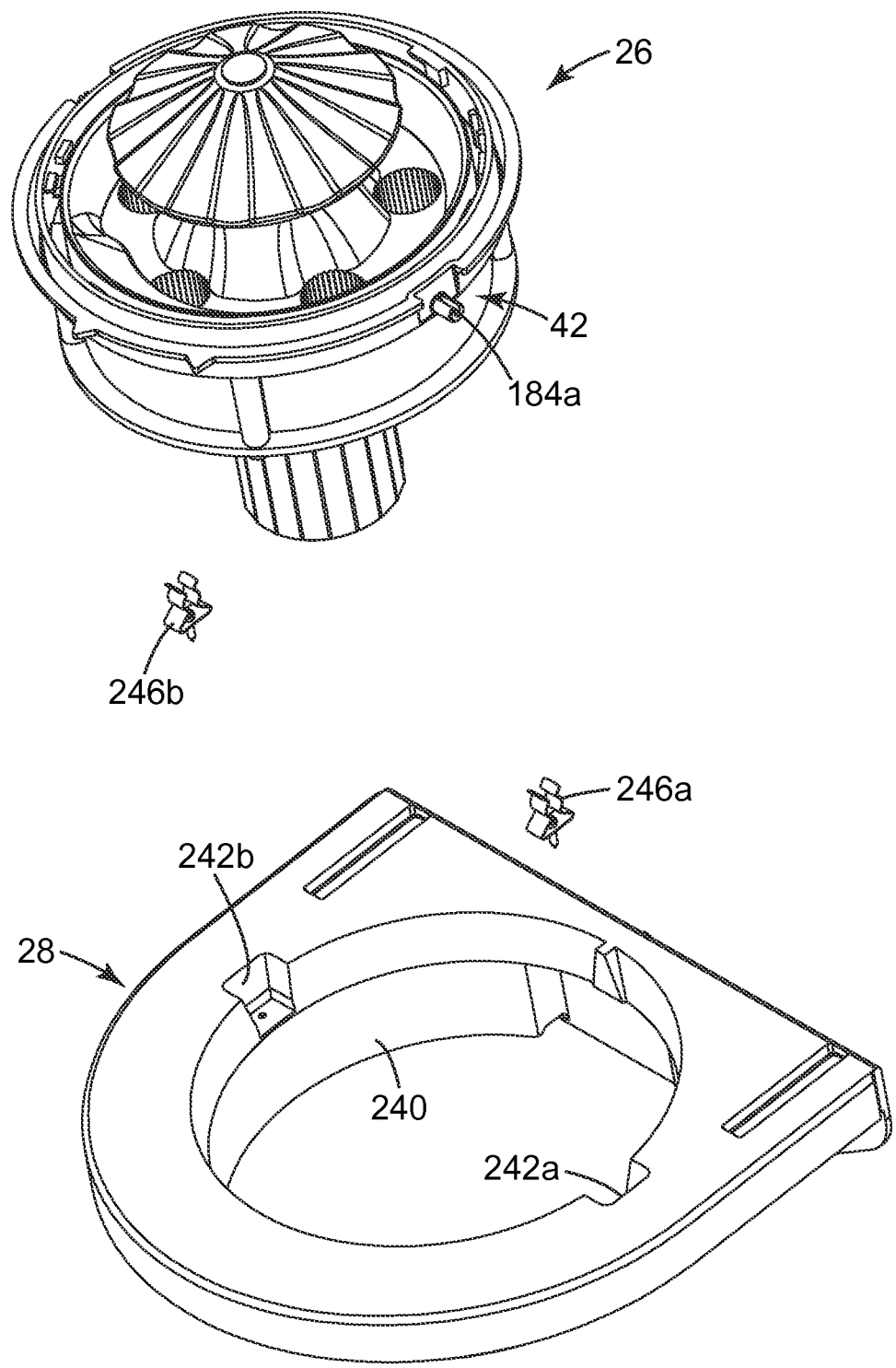
FIG. 11A is a exploded, perspective view of a portion of the dispenser of FIG. 1A, including the dispensing mechanism and a frame.
Figure 11B:
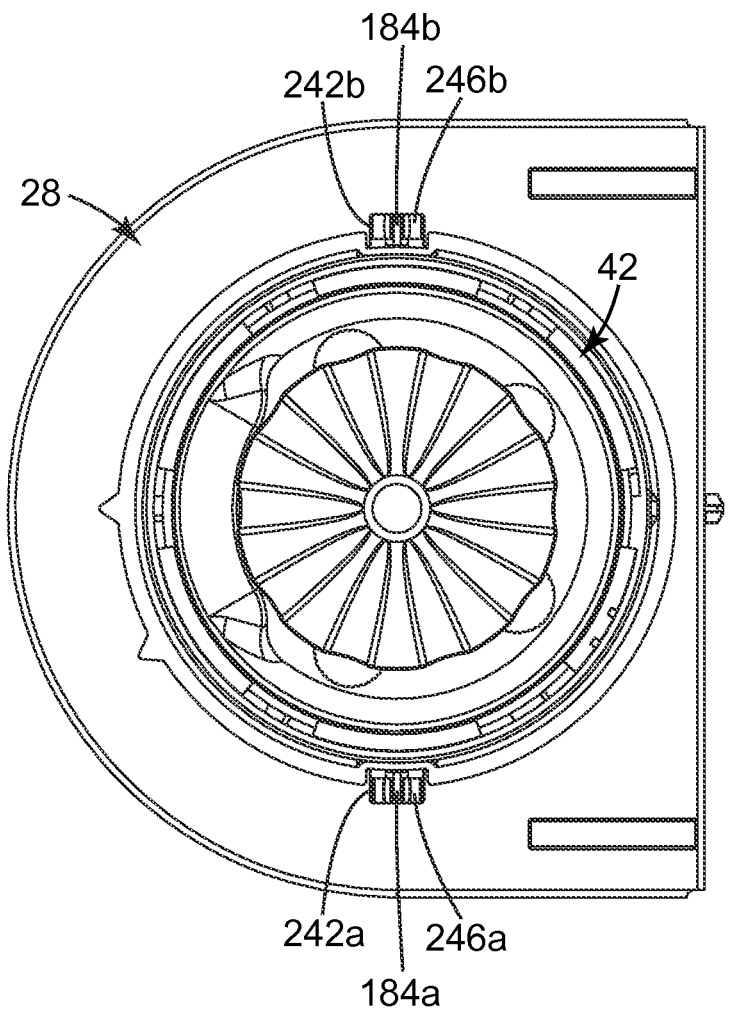
FIG. 11B is a top view of the components of FIG. 11A upon final assembly.

As indicated above, manual operation of the dispensing mechanism 26 generally entails user-caused rotation of the index body 40 relative to the housing 42 (and thus relative to the plate 44 that is otherwise affixed to the housing 42). With this in mind, the dispensers of the present disclosure can include components that spatially retain the housing 42 at a desired location and in a manner that spatially "holds" the housing 42 during rotation of the index body 40. For example, FIG. 1A illustrates the frame 28 provided as part of the stand 30. As shown in FIG. 11A, the frame 28 forms a passage 240 that is sized and shaped to receive the housing 42. In this regard, the frame 28 is optionally configured, in tandem with the housing 42, such that the housing 42 (and thus the dispensing mechanism 26) can be removably mounted to the passage 240. Moreover, the frame 28 and the housing 42 incorporate complimentary features that fix the housing 42 to the frame 28 such that the housing 42 cannot rotate relative to the frame 28. For example, the frame 28 can form opposing cavities 242a, 242b sized and shaped to receive a respective one of the pins 184a, 184b (one of which is visible in FIG. 11A) provided with the housing 42. With additional reference to FIG. 11B, upon placement of the pins 184a, 184b within the corresponding cavity 242a, 242b, the housing 42 is thus supported by the frame 28, and cannot freely rotate relative to the frame 28. In some embodiments, a clip assembly 246a, 246b can be assembled to each of the pins 184a, 184b, respectively, and is configured to achieve a more robust, press fittype coupling between the pins 184*a*, 184*b* and the frame 28. Alternatively, a wide variety of other mounting constructions are equally acceptable.

Figure 12:
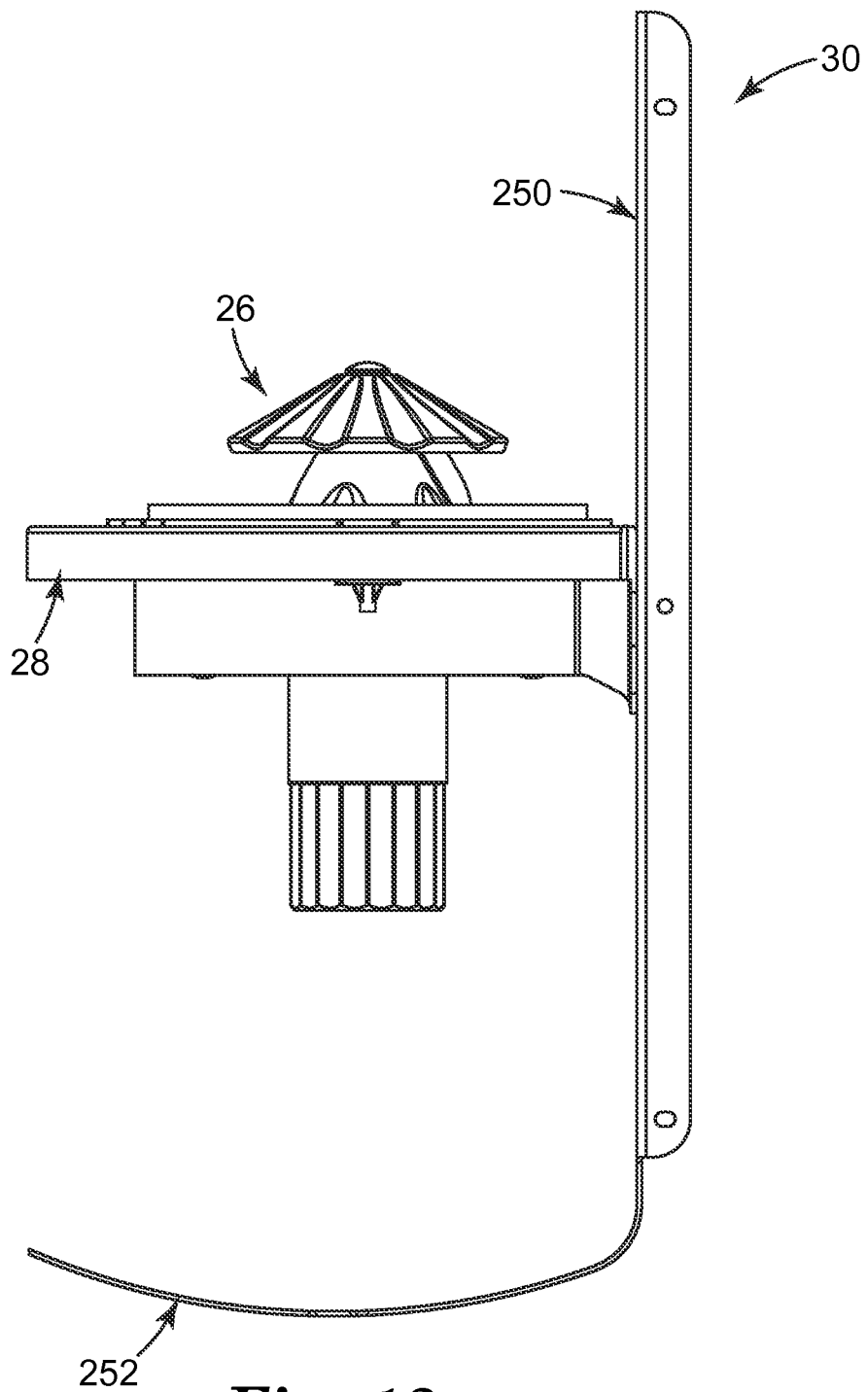
FIG. 12 is a side view of a portion of the dispenser of FIG. 1A, including the dispensing mechanism assembled to a stand.

In some embodiments, the frame 28 can be directly assembled to a surface of interest (e.g., a vertical wall). In other embodiments, the frame 28 can be provided as part of the stand 30 that otherwise incorporates additional, optional structures that serve to support the frame 28 as shown in FIG. 1A. For example, the stand 30 can include or form a back wall 250 and a bottom wall 252. The frame 28 is coupled to the back wall 250 and arranged such that the bottom wall 252 projects underneath the frame 28. In some embodiments, the back wall 250 can incorporate various features that promote assembly to a vertical surface (e.g., a wall), for example mounting shells 254. Where provided, the bottom wall 252 serves as a catch for earplugs (not shown) released from the dispensing mechanism 26, and can include or form water drainage holes 256. The bottom wall 252 can have the curved shape shown (e.g., with embodiments in which the stand 30 is assembly to a separate structure so as to retain the bottom wall 252 above a floor or other surface), or can be flattened. In other configurations, the bottom wall 252 can be omitted. Final mounting of the dispensing mechanism 26 to the stand 30 is shown in FIG. 12.

Returning to FIGS. 1A and 1B, the dispensing unit 22 can optionally be further protected from the environment by the cover 24. The cover 24 includes or defines a front panel 260 and opposing side panels 262*a*, 262*b*. The front panel 260 forms an access opening 264 and a fill level opening 266. The side panel 262*a*, 262*b* are sized and shaped for assembly to the back wall 250 of the stand 30, with the access opening 264 being sized and shaped to facilitate insertion of a user's hand. The fill level opening 266 is located to promote viewing of components within the cover 24 as described below.

Figure 13:
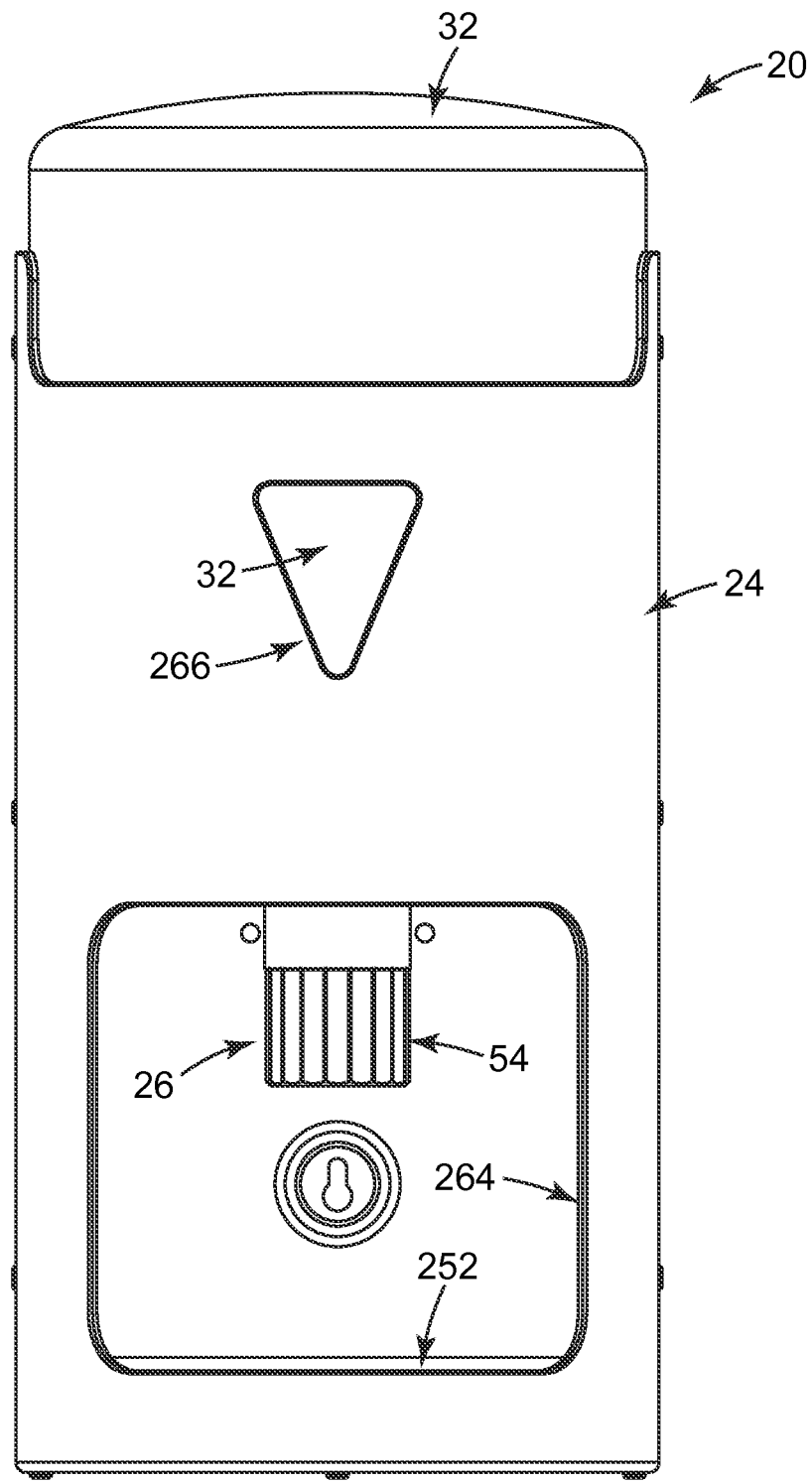
FIG. 13 is a front view of the dispenser of FIG. 1A upon final assembly.

For example, FIG. 13 depicts the dispenser 20 upon final assembly, including mounting of the container 32 to the dispensing mechanism 26 (referenced generally). A user can obtain individual earplugs (not shown) by inserting his or her hand through the access opening 264 and grasping the handle 54. The user then rotates the handle 54 to cause a single earplug to be dispensed into the user's hand as described above. Notably, the cover 24 serves to protect the so-dispensed earplug from the surrounding environment (e.g., wind, rain, etc.). Moreover, the drainage holes 256 (hidden in FIG. 13, but shown in FIG. 1A) in the bottom wall 252 allow any water (e.g., rain) entering the access opening 264 to readily drain away. Thus, the dispenser 20 is highly amenable for installation at a plethora of different locations, including outdoor use. Finally, the fill level opening 266 is generally aligned with a portion of the container 32, thus allowing a user to visually estimate the quantity of earplugs remaining within the container 32.

The disposable earplug dispensing mechanisms and related earplug dispensers of the present disclosure provide a marked improvement over previous designs. The dispensing mechanism is easy to manually operate, and accurately dispenses earplugs from a bulk supply on an individual basis with minimal occurrences of jamming. Optional features, such as the low surface energy bores, the shield, the earplug guides, etc., promote consistent interface with compressible, tacky disposable earplugs.

Although the present invention has been described with reference to preferred embodiments, workers skilled in the art will recognize that changes can be made in form and detail without departing from the spirit and scope of the present invention.

What is claimed is:

1. A manually operable dispenser for dispensing earplugs from a container of earplugs, the dispenser comprising:
   a housing forming an opening for receiving earplugs from a container;
   an index body including:
      a handle terminating at a lower end,
      a hub projecting radially outwardly from the handle opposite the lower end, the hub forming an upper major face, a lower major face opposite the upper major face, and a plurality of circumferentially arranged bores each configured to receive an earplug,
      a guide cone projecting from the upper major face of the hub, the guide cone tapering in diameter from the upper major face of the hub to a leading end of the guide cone,
      a shield including a base disposed above the leading end opposite the upper major face and a shield wall projecting radially outwardly from the base to a perimeter edge having a diameter greater than a diameter of the leading end,
         wherein the shield and the handle are rotationally affixed and wherein the shield is cone-shaped with an open side of the shield facing toward the upper major face of the hub;
         wherein the hub is mounted within the opening of the housing;
   and
   a plate proximate the lower major face of the hub, the plate forming a dispensing aperture;
      wherein the dispenser is configured such that a manually-applied rotational force at the handle selectively aligns individual ones of the bores with the dispensing aperture;
      and wherein the housing further comprises:
         a sleeve forming the opening, an upper end, a lower end, and a central axis;
         a guide wall projecting from the upper end in a direction of the lower end to an inner edge, the guide wall tapering in diameter relative to the central axis from the upper end to the inner edge; and
         a barrier member projecting radially inwardly from the guide wall, the barrier member having an arc angle less than 360 degrees,
      and wherein upon final assembly the upper major face of the hub is proximate the inner edge of the guide wall of the sleeve, wherein a diameter of the inner edge is greater than an outer diameter collectively defined by the plurality of bores; and the barrier member is located at a radial distance relative to the central axis that is greater than a diameter of an imaginary circle collectively defined by centerpoints of the plurality of bores.

2. The dispenser of claim 1, wherein the hub forms a platform defining the upper major face of the hub, and further wherein the guide cone projects upwardly from the platform and forms a plurality of troughs, respective ones of the troughs being aligned with a corresponding one of the bores, and even further wherein the guide cone forms a plurality of partitions, respective ones of which project into a spacing between a corresponding spacing between a pair of circumferentially adjacent ones of the bores.

3. The dispenser of claim 1, wherein an outer diameter of the shield wall is not less than a diameter of an imaginary circle collectively defined connected by centerpoints of the bores.

4. The dispenser of claim 1, wherein the shield wall defines a top surface opposite the guide cone, and further wherein the top surface projects radially outwardly and longitudinally downwardly in a direction of the upper major face in extension from the base to the perimeter edge.

5. The dispenser of claim 4, wherein the top surface forms a plurality of contours.

6. The dispenser of claim 1, wherein handle, the guide cone and the shield define a common longitudinal axis.

7. The dispenser of claim 1, wherein the barrier member is longitudinally aligned with the dispensing aperture.

8. The dispenser of claim 1, wherein the shield and the hub combine to define a chamber for receiving earplugs, and further wherein the guide cone is configured to guide individual earplugs from the chamber into respective ones of the bores.

9. The dispenser of claim 1, further comprising:
a container for containing a supply of earplugs, the container forming a neck terminating at an open end and a closed end opposite the open end;
wherein the housing is configured to selectively receive the open end in a mounted state;
and further wherein in the mounted state, the dispenser defines:
a first chamber between the shield wall and the upper major face,
a second chamber between the shield wall and the closed end.

10. The dispenser of claim 9, wherein the first chamber is open to the second chamber.

11. The dispenser of claim 9, wherein a diameter of a perimeter edge of the shield wall is less than a diameter of the open end of the container.

12. The dispenser of claim 9, wherein the dispenser is configured such that a first portion of a supply of earplugs provided with the container is located in the first chamber and a second portion of the supply of earplugs is supported in the second chamber by the shield.

13. The dispenser of claim 12, wherein the dispenser is configured that such earplugs of the second portion of the supply of earplugs replenish earplugs dispensed from the first chamber via gravity.

14. The dispenser of claim 1, wherein the dispenser is configured such that individual earplugs within the housing are induced by gravity into respective ones of the bores, and an earplug within a respective one of the bores is induced by gravity into the dispensing aperture upon alignment of the respective one of the bores with the dispensing aperture.

15. The dispenser of claim 1, further comprising:
a stand maintaining a frame sized to support the housing above a surface such that upon assembly of the housing to the frame, the handle extends below the frame and the housing is held stationary with rotation of the handle.

16. The dispenser of claim 1, wherein the guide wall and the guide cone are configured to guide individual earplugs in a lengthwise fashion into respective ones of the bores.

* * * * *